(12) United States Patent
Li

(10) Patent No.: US 8,273,751 B2
(45) Date of Patent: Sep. 25, 2012

(54) ORGANIC COMPOUNDS

(75) Inventor: Peng Li, New York, NY (US)

(73) Assignee: Takeda Pharmaceutical Company Limited, Chuo-Ku, Osaka (JP)

( * ) Notice: Subject to any disclaimer, the term of this patent is extended or adjusted under 35 U.S.C. 154(b) by 48 days.

(21) Appl. No.: 12/746,236

(22) PCT Filed: Dec. 6, 2008

(86) PCT No.: PCT/US2008/013411
§ 371 (c)(1),
(2), (4) Date: Jun. 4, 2010

(87) PCT Pub. No.: WO2009/075784
PCT Pub. Date: Jun. 18, 2009

(65) Prior Publication Data
US 2010/0273754 A1    Oct. 28, 2010

Related U.S. Application Data

(60) Provisional application No. 61/012,040, filed on Dec. 6, 2007.

(51) Int. Cl.
*C07D 239/70*    (2006.01)
*C07D 487/00*    (2006.01)
(52) U.S. Cl. .................................. 514/257; 544/246
(58) Field of Classification Search .................. 514/257; 544/246
See application file for complete search history.

(56) References Cited

U.S. PATENT DOCUMENTS

| | | | |
|---|---|---|---|
| 5,294,612 A | 3/1994 | Bacon et al. | |
| 5,393,755 A | 2/1995 | Neustadt et al. | |
| 5,939,419 A | 8/1999 | Tulshian | |
| 6,013,621 A | 1/2000 | Nishi et al. | |
| 6,492,371 B2 | 12/2002 | Roylance | |
| 6,756,373 B1 | 6/2004 | Allerton et al. | |
| 6,969,719 B2 | 11/2005 | Asberom et al. | |
| 2003/0162782 A1 | 8/2003 | Grossman et al. | |
| 2004/0259792 A1 | 12/2004 | Palmer et al. | |
| 2008/0176961 A1 | 7/2008 | Greengard et al. | |
| 2008/0188492 A1* | 8/2008 | Li et al. .......... | 514/257 |
| 2008/0193964 A1 | 8/2008 | Greengard et al. | |
| 2008/0194592 A1 | 8/2008 | Mates et al. | |
| 2010/0087450 A1 | 4/2010 | Mates et al. | |
| 2010/0173878 A1 | 7/2010 | Li et al. | |
| 2010/0273753 A1 | 10/2010 | Li et al. | |
| 2011/0237561 A1 | 9/2011 | Li et al. | |
| 2011/0245214 A1 | 10/2011 | Li et al. | |
| 2011/0281832 A1 | 11/2011 | Li et al. | |
| 2011/0312978 A1 | 12/2011 | Davis et al. | |
| 2012/0053190 A1* | 3/2012 | Fienberg et al. ........... | 514/262.1 |

FOREIGN PATENT DOCUMENTS

| | | |
|---|---|---|
| DE | 19931206 | 1/2001 |
| EP | 0201188 | 12/1986 |
| EP | 0911333 A1 | 4/1999 |
| KR | 10-1991-0006866 | 9/1991 |
| WO | WO 91/19717 | 12/1991 |
| WO | WO 94/19351 | 9/1994 |
| WO | WO 98/46606 | 10/1998 |
| WO | WO 98/52568 | 11/1998 |
| WO | WO 03/002567 | 1/2003 |
| WO | WO 03/020702 | 3/2003 |
| WO | WO 03/042216 | 5/2003 |
| WO | WO 2007/143705 | 12/2007 |
| WO | WO 2009/073210 | 6/2009 |
| WO | WO 2011/043816 | 4/2011 |
| WO | WO 2011/153129 | 12/2011 |
| WO | WO 2011/153135 | 12/2011 |
| WO | WO 2011/153136 | 12/2011 |
| WO | WO 2011/153138 | 12/2011 |

OTHER PUBLICATIONS

Nishi, et al. Advanced Research on Dopamine Signaling to Develop Drugs for the Treatment of Mental Disorders: Biochemical and Behavioral Profiles of Phosphodiesterase Inhibition in Dopaminergic Neurotransmission, J. Pharmacol. Sci., 114, 6-16 (2010).*
Ahn, H. et al., "Potent Tetracyclic Guanine Inhibitors of PDE1 and PDE5 Cyclic Guanosine Monophosphate Phosphodiesterases with Oral Antihypertensive Activity", J. Med. Chem., 1997, 40(14), pp. 2196-2210.
Banker, G.S. et al., Modern Pharmaceutics, Marcel Dekker, New York, 1996.
U.S. Appl. No. 12/517,945, Dec. 15, 2007, Feinberg et al.
Bender, A.T. et al., "Cyclic Nucleotide Phosphodiesterases: Molecular Regulation to Clinical Use", Pharmcol. Rev., 2006, 58, pp. 488-520.
Dewald, H.A. et al., "Synthesis and Potential Antipsychotic Activity of 1*H*-Imidazo[1,2-c]pyrazolo[3,4-*e*]pyrimidines", J. Med. Chem., 1988, 31, pp. 454-461.
Fienberg, A.A. et al., "DARPP-32: Regulator of the Efficacy of Dopaminergic Neurotransmission", Science, 1998, 281, pp. 838-842.
Greengard, P. et al., "Beyond the Dopamine Receptor: the DARPP-32/Protein Phosphatase-1 Cascade", Neuron, 1999, 23, pp. 435, 447.
Han, P. et al., "The Calcium/Calmodulin-dependent Phosphodiesterase PDE1C Down-regulates Glucose-induced Insulin Secretion", J. Bio. Chem., 1999, 274(32), pp. 22337-22344.
Jiang, M. et al., "Chemoenzymatic Asymmetric Total Synthesis of Phosphodiesterase Inhibitors: Preparation of a Polycyclic Pyrazolo[3,4-*d*]pyrimidine from an Acylnitroso Diels-Alder Cycloadduct-Derived Aminocyclopentenol", J. Org. Chem., 2005, 70, pp. 2824-2827.
Mani, S.K. et al., "Requirement for DARPP-32 in Progesterone-Facilitated Sexual Receptivity in Female Rats and Mice", Science, 2000, 287, p. 1053.
Murray, F. et al., "Expression and activity of cAMP phosphodiesterase isoforms in pulmonary artery smooth muscle cells from patients with pulmonary hypertension: role for PDE1", Am. J. Physiol. Lung Cell Mol. Physiol., 2007, 292, pp. L294-L303.
Polli, J.W. et al., "Expression of a Calmodulin-Dependent Phosphodiesterase Isoform (PDE1B1) Correlates With Brain Regions Having Extensive Dopaminergic Innervation", 1994, The Journal of Neuroscience, 14, pp. 1251-1261.

(Continued)

*Primary Examiner* — Erich A Leeser
(74) *Attorney, Agent, or Firm* — Hoxie & Associates LLC

(57) ABSTRACT

1- or 2-substituted (6aR,9aS)-3-(phenylamino)-5-6a,7,8,9, 9a-hexahydro-5-methyl-cyclopent[4,5]imidazo[1,2-a]pyrazolo[4,3-e]pyrimidin-4(1H or, 2H)-one compounds of Formula (I), processes for their production, their use as pharmaceuticals and pharmaceutical compositions comprising them.

3 Claims, No Drawings

OTHER PUBLICATIONS

Reed, T.M. et al., "Phosphodiesterase 1B Knock-Out Mice Exhibit Exaggerated Locomotor Hyperactivity and DARPP-32 Phosphorylation in Response to Dopamine Agonists and Display Impaired Spatial Learning", The Journal of Neuroscience, 2002, 22(12), pp. 5188-5197.

Rybalkin, S.D. et al., "Cyclic GMP Phosphodiesterases and Regulation of Smooth Muscle Function", Circ. Res., 2003, 93, pp. 280-291.

Shimizu, K. et al., "Calmodulin-Dependent Cyclic Nucleotide Phosphodiesterase (PDE1) is a Pharmacological Target of Differentiation-Inducing Factor-1, an Antitumor Agent Isolated from Dictyostelium" Cancer Research, 2004, 64, pp. 2568-2571.

Vatter, S. et al., Differential Phosphodiesterase Expression and Cytosolic Ca in Human CNS Tumour Cells and in Non-Malignant and Malignant Cells of Rat Origin, J. of Neurochemistry, 2005, 93, pp. 321-329.

Wolff, M.E., Burger's Medicinal Chemistry and Drug Discovery, Fifth Ed., vol. 1: Principles and Practice, John Wiley & Sons, 1995, 975.

Xia, Y. et al., Synthesis and Evaluation of Polycyclic Pyrazolo[34-d]pyrimidines as PDE1 and PDE5 cGMP Phosphodiesterase Inhibitors, Journal Medicinal Chemistry, 1997, 40, pp. 4372-4377.

Office Actions for U.S. Appl. No. 11/916,761: (Restriction Requirement, Non-Final Office Action, Final Rejection Office Action, Advisory Action).

U.S. Appl. No. 13/133,082, Li et al.
U.S. Appl. No. 13/132,955, Li et al.
U.S. Appl. No. 13/133,147, Li et al.
U.S. Appl. No. 13/319,807, Fienberg et al.

* cited by examiner

ORGANIC COMPOUNDS

CROSS REFERENCE TO RELATED APPLICATIONS

This application is a United States National Stage Application under 35 USC §371 of PCT/US2008/013411, filed Dec. 6, 2008, which claims priority from U.S. Provisional application No. 61/012,040, filed Dec. 6, 2007, the contents of each of which are hereby incorporated by reference.

STATEMENT REGARDING GOVERNMENT FUNDING

This invention was made, in part, with government support under Grant. No. 2R44MH067488 awarded by NIMH and Grant No. DAMD-17-03-1-0396 awarded by USAMRMC. The government has certain rights in the invention.

TECHNICAL FIELD

The present invention relates to 1- or 2-substituted (6aR*, 9aS*)-3-(phenylamino)-5-6a,7,8,9,9a-hexahydro-5-methyl-cyclopent[4,5]imidazo[1,2-a]pyrazolo[4,3-e]pyrimidin-4 (1H or 2H)-one compounds, preferably 1- or 2-substituted (6aR,9aS) (phenylamino)-5-6a,7,8,9,9a-hexahydro-5-methyl-cyclopent[4,5]imidazo[1,2-a]pyrazolo[4,3-e]pyrimidin-4(1H or 2H)-one compounds of Formula I as described below, processes for their production, their use as pharmaceuticals and pharmaceutical compositions comprising them. Of particular interest are novel compounds useful as inhibitors of phosphodiesterase 1 (PDE1), e.g., in the treatment of diseases involving disorders of the dopamine D1 receptor intracellular pathway, such as Parkinson's disease, depression, narcolepsy, damage to cognitive function, e.g., in schizophrenia, or disorders that may be ameliorated through enhanced progesterone-signaling pathway, e.g., female sexual dysfunction.

BACKGROUND OF THE INVENTION

Eleven families of phosphodiesterases (PDEs) have been identified but only PDEs in Family I, the $Ca^{2+}$-calmodulin-dependent phosphodiesterases (CaM-PDEs), have been shown to mediate both the calcium and cyclic nucleotide (e.g. cAMP and cGMP) signaling pathways. The three known CaM-PDE genes, PDE1A, PDE1B, and PDE1C, are all expressed in central nervous system tissue. PDE1A is expressed throughout the brain with higher levels of expression in the CA1 to CA3 layers of the hippocampus and cerebellum and at a low level in the striatum. PDE1A is also expressed in the lung and heart. PDE1B is predominately expressed in the striatum, dentate gyrus, olfactory tract and cerebellum, and its expression correlates with brain regions having high levels of dopaminergic innervation. Although PDE1B is primarily expressed in the central nervous system, it may be detected in the heart. PDE1C is primarily expressed in olfactory epithelium, cerebellar granule cells, and striatum. PDE1C is also expressed in the heart and vascular smooth muscle.

Cyclic nucleotide phosphodiesterases decrease intracellular cAMP and cGMP signaling by hydrolyzing these cyclic nucleotides to their respective inactive 5'-monophosphates (5'AMP and 5'GMP). CaM-PDEs play a critical role in mediating signal transduction in brain cells, particularly within an area of the brain known as the basal ganglia or striatum. For example, NMDA-type glutamate receptor activation and/or dopamine D2 receptor activation result in increased intracellular calcium concentrations, leading to activation of effectors such as calmodulin-dependent kinase II (CaMKII) and calcineurin and to activation of CaM-PDEs, resulting in reduced cAMP and cGMP. Dopamine D1 receptor activation, on the other hand, leads to activation of nucleotide cyclases, resulting in increased cAMP and cGMP. These cyclic nucleotides in turn activate protein kinase A (PKA; cAMP-dependent protein kinase) and/or protein kinase G (PKG; cGMP-dependent protein kinase) that phosphorylate downstream signal transduction pathway elements such as DARPP-32 (dopamine and cAMP-regulated phosphoprotein) and cAMP responsive element binding protein (CREB). Phosphorylated DARPP-32 in turn inhibits the activity of protein phosphates-1 (PP-1), thereby increasing the state of phosphorylation of substrate proteins such as progesterone receptor (PR), leading to induction of physiologic responses. Studies in rodents have suggested that inducing cAMP and cGMP synthesis through activation of dopamine D1 or progesterone receptor enhances progesterone signaling associated with various physiological responses, including the lordosis response associated with receptivity to mating in some rodents. See Mani, et al., Science (2000) 287: 1053, the contents of which are incorporated herein by reference.

CaM-PDEs can therefore affect dopamine-regulated and other intracellular signaling pathways in the basal ganglia (striatum), including but not limited to nitric oxide, noradrenergic, neurotensin, CCK, VIP, serotonin, glutamate (e.g., NMDA receptor, AMPA receptor), GABA, acetylcholine, adenosine (e.g., A2A receptor), cannabinoid receptor, natriuretic peptide (e.g., ANP, BNP, CNP), DARPP-32, and endorphin intracellular signaling pathways.

Phosphodiesterase (PDE) activity, in particular, phosphodiesterase 1 (PDE1) activity, functions in brain tissue as a regulator of locomotor activity and learning and memory. PDE1 is a therapeutic target for regulation of intracellular signaling pathways, preferably in the nervous system, including but not limited to a dopamine D1 receptor, dopamine D2 receptor, nitric oxide, noradrenergic, neurotensin, CCK, VIP, serotonin, glutamate (e.g., NMDA receptor, AMPA receptor), GABA, acetylcholine, adenosine (e.g., A2A receptor), cannabinoid receptor, natriuretic peptide (e.g., ANP, BNP, CNP), endorphin intracellular signaling pathway and progesterone signaling pathway. For example, inhibition of PDE should act to potentiate the effect of a dopamine D1 agonist by protecting cGMP and cAMP from degradation, and should similarly inhibit dopamine D2 receptor signaling pathways, by inhibiting PDE1 activity. Chronic elevation in intracellular calcium levels is linked to cell death in numerous disorders, particularly in neurodegerative diseases such as Alzheimer's, Parkinson's and Huntington's Diseases and in disorders of the circulatory system leading to stroke and myocardial infarction. PDE1 inhibitors are therefore potentially useful in diseases characterized by reduced dopamine D1 receptor signaling activity, such as Parkinson's disease, restless leg syndrome, depression, narcolepsy and cognitive impairment. PDE1 inhibitors are also useful in diseases that may be alleviated by the enhancement of progesterone-signaling such as female sexual dysfunction.

There is thus a need for compounds that selectively inhibit PDE1 activity, especially PDE1B activity.

SUMMARY OF THE INVENTION

The invention provides 1- or 2-substituted (6aR*,9aS*)-3-(phenylamino)-5-6a,7,8,9,9a-hexahydro-5-methyl-cyclopent[4,5]imidazo[1,2-a]pyrazolo[4,3-e]pyrimidin-4(1H or 2H)-one compounds, preferably 1- or 2-substituted (6aR, 9aS)-3-(phenylamino)-5-6a,7,8,9,9a-hexahydro-5-methyl-cyclopent[4,5]imidazo[1,2-a]pyrazolo[4,3-e]pyrimidin-4 (1H or 2H)-ones, of formula Q

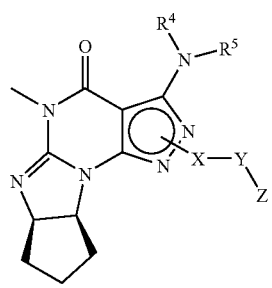

Formula Q wherein
- (i) X is $C_{1-6}$alkylene (e.g., methylene, ethylene or prop-2-yn-1-ylene);
- (ii) Y is a single bond, alkynylene (e.g., —C≡C—), arylene (e.g., phenylene) or heteroarylene (e.g., pyridylene);
- (iii) Z is H, aryl (e.g., phenyl), heteroaryl (e.g., pyridyl, e.g., pyrid-2-yl), halo (e.g., F, Br, Cl), halo$C_{1-6}$alkyl (e.g., trifluoromethyl), —C(O)—$R^1$, —N($R^2$)($R^3$), or $C_{3-7}$cycloalkyl optionally containing at least one atom selected from a group consisting of N or O (e.g., cyclopentyl, cyclohexyl, tetrahydro-2H-pyran-4-yl, or morpholinyl);
- (iv) $R^1$ is $C_{1-6}$alkyl, halo$C_{1-6}$alkyl, —OH or —O$C_{1-6}$alkyl (e.g., —OCH$_3$);
- (v) $R^2$ and $R^3$ are independently H or $C_{1-6}$alkyl;
- (vi) $R^4$ and $R^5$ are independently H, $C_{1-6}$alky or aryl (e.g., phenyl) optionally substituted with one or more halo (e.g., fluorophenyl, e.g., 4-fluorophenyl), hydroxy (e.g., hydroxyphenyl, e.g., 4-hydroxyphenyl or 2-hydroxyphenyl) or $C_{1-6}$alkoxy;
- (vii) wherein X, Y and Z are independently and optionally substituted with one or more halo (e.g., F, Cl or Br), $C_{1-6}$alkyl (e.g., methyl), halo$C_{1-6}$alkyl (e.g., trifluoromethyl), for example, Z is heteroaryl, e.g., pyridyl substituted with one or more halo (e.g., 6-fluoropyrid-2-yl, 5-fluoropyrid-2-yl, 6-fluoropyrid-2-yl, 3-fluoropyrid-2-yl, 4-fluoropyrid-2-yl, 4,6-dichloropyrid-2-yl), halo$C_{1-6}$alkyl (e.g., 5-trifluoromethylpyrid-2-yl) or $C_{1-6}$-alkyl (e.g., 5-methylpyrid-2-yl), or Z is aryl, e.g., phenyl, substituted with one or more halo (e.g., 4-fluorophenyl), in free, salt or prodrug form. In a further embodiment, the invention provides a compound of Formula Q, which includes the proviso that when X is an unsubstituted methylene, Y is phenylene or heteroarylene, and Z is aryl, heteroaryl, haloalkyl or cycloalkyl, then Z is substituted with at least one halo (e.g., fluoro, chloro, bromo) or alkyl (e.g., methyl, ethyl) group.

The invention further provides compounds of Formula Q as described above as follows:

1.1 Formula Q, wherein X is $C_{1-6}$alkylene (e.g., methylene, ethylene or prop-2-yn-1-ylene) optionally substituted with one or more halo (e.g., F, Cl or Br), $C_{1-6}$alkyl (e.g., methyl), halo$C_{1-6}$alkyl (e.g., trifluoromethyl);

1.2 Formula Q or 1.1, wherein X is methylene or ethylene optionally substituted with one or more halo (e.g., F, Cl or Br), $C_{1-6}$alkyl (e.g., methyl), halo$C_{1-6}$alkyl (e.g., trifluoromethyl);

1.3 Formula Q, 1.1 or 1.2, wherein X is methylene optionally substituted with one or more halo (e.g., F, Cl or Br), $C_{1-6}$alkyl (e.g., methyl), halo$C_{1-6}$alkyl (e.g., trifluoromethyl);

1.4 Formula Q, 1.1, 1.2 or 1.3, wherein X is methylene substituted with bromo;

1.5 Formula Q, 1.1, 1.2, 1.3 or 1.4, wherein X is ethylene;

1.6 Formula Q or any of 1.1-1.5, wherein X is prop-2-yn-1-ylene;

1.7 Formula Q or any of 1.1-1.6, wherein Y is a single bond, arylene (e.g., phenylene) or heteroarylene (e.g., pyridylene) optionally substituted with one or more halo (e.g., F, Cl or Br), $C_{1-6}$alkyl (e.g., methyl), halo$C_{1-6}$alkyl (e.g., trifluoromethyl);

1.8 Formula Q or any of 1.1-1.7, wherein Y is arylene (e.g., phenylene) optionally substituted with one or more halo (e.g., F, Cl or Br), $C_{1-6}$alkyl (e.g., methyl), halo$C_{1-6}$alkyl (e.g., trifluoromethyl);

1.9 Formula Q or any of 1.1-1.8 wherein Y is phenylene optionally substituted with fluoro at the 3 or 5-position of the phenylene ring;

1.10 Formula Q or any of 1.1-1.9, wherein Y is phenylene;

1.11 Formula Q or any of 1.1-1.7, wherein Y is heteroarylene (e.g., pyridylene) optionally substituted with one or more halo (e.g., F, Cl or Br), $C_{1-6}$alkyl (e.g., methyl), halo$C_{1-6}$alkyl (e.g., trifluoromethyl);

1.12 Formula Q or any of 1.1-1.7, wherein Y is a single bond;

1.13 Formula Q or any of 1.1-1.7, wherein Y is heteroaryl (e.g., pyrid-2-yl);

1.14 Formula Q or any of 1.1-1.13, wherein Z is H, aryl (e.g., phenyl), heteroaryl (e.g., pyridyl, e.g., pyrid-2-yl), halo (e.g., F, Br, Cl), halo$C_{1-6}$alkyl (e.g., trifluoromethyl), —C(O)—$R^1$, —N($R^2$)($R^3$), or $C_{3-7}$cycloalkyl optionally containing at least one atom selected from a group consisting of N or O (e.g., cyclopentyl, cyclohexyl, tetrahydro-2H-pyran-4-yl, or morpholinyl), wherein said aryl and heteroaryl are optionally substituted with one or more halo (e.g., F, Cl or Br), $C_{1-6}$alkyl (e.g., methyl), halo$C_{1-6}$alkyl (e.g., trifluoromethyl);

1.15 Formula Q or any of 1.1-1.14, wherein Z is $C_{3-7}$cycloalkyl optionally containing at least one atom selected from a group consisting of N or O (e.g., cyclopentyl, cyclohexyl, tetrahydro-2H-pyran-4-yl, morpholinyl);

1.16 Formula Q or any of 1.1-1.15, wherein Z is cyclopentyl;

1.17 Formula Q or any of 1.1-1.15, wherein Z is tetrahydro-2H-pyran-4-yl;

1.18 Formula Q or any of 1.1-1.14, wherein Z is heteroaryl (e.g., pyridyl, e.g., pyrid-2-yl) optionally substituted with one or more halo (e.g., F, Cl or Br), $C_{1-6}$alkyl (e.g., methyl), halo$C_{1-6}$alkyl (e.g., trifluoromethyl);

1.19 Formula Q or any of 1.1-1.14 or 1.18, wherein Z is pyridyl;

1.20 Formula Q or any of 1.1-1.14 or 1.18, wherein Z is pyrid-2-yl;

1.21 Formula Q or any of 1.1-1.14 or 1.18, wherein Z is 3-fluoropyrid-2-yl;

1.22 Formula Q or any of 1.1-1.14 or 1.18, wherein Z is 4-fluoropyrid-2-yl;

1.23 Formula Q or any of 1.1-1.14 or 1.18, wherein Z is 5-fluoropyrid-2-yl;

1.24 Formula Q or any of 1.1-1.14 or 1.18, wherein Z is 6-fluoropyrid-2-yl;

1.25 Formula Q or any of 1.1-1.14 or 1.18, wherein Z is heteroaryl, e.g., pyridyl, optionally substituted with one or more haloC$_{1-6}$alkyl (e.g., 5-trifluoromethylpyrid-2-yl;

1.26 Formula Q or any of 1.1-1.14 or 1.18, wherein Z is 5-trifluoromethylpyrid-2-yl;

1.27 Formula Q or any of 1.1-1.14 or 1.18, wherein Z is heteroaryl, e.g., pyridyl, optionally substituted with one or more C$_{1-6}$alkyl (e.g., 5-methylpyrid-2-yl);

1.28 Formula Q or any of 1.1-1.14 or 1.18, wherein Z is 5-methylpyrid-2-yl;

1.29 Formula Q or any of 1.1-1.14, wherein Z is haloC$_{1-6}$ alkyl (e.g., trifluoromethyl);

1.30 Formula Q or any of 1.1-1.14 or 1.29, wherein Z is trifluoromethyl;

1.31 Formula Q or any of 1.1-1.14 wherein Z is aryl, e.g., phenyl, optionally substituted with one or more halo (e.g., 4-fluorophenyl), haloC$_{1-6}$alkyl or C$_{1-6}$alkyl;

1.32 Formula Q or any of 1.1-1.14, wherein Z is aryl (e.g., phenyl) one or more halo (e.g., 4-fluorophenyl), haloC$_{1-6}$ alkyl or C$_{1-6}$alkyl;

1.33 Formula Q or any of 1.1-1.14 or 1.36, wherein Z is phenyl;

1.34 Formula Q or any of 1.1-1.14 or 1.31 wherein Z is 4-fluorophenyl;

1.35 Formula Q or any of 1.1-1.14, wherein Z is —C(O)—R$^1$ and R$^1$ is C$_{1-6}$alkyl (e.g., methyl), haloC$_{1-6}$alkyl (e.g., trifluoromethyl), —OH or —OC$_{1-6}$alkyl (e.g., —OCH$_3$);

1.36 Formula Q or any of 1.1-1.14 or 1.29, wherein Z is —C(O)—R$^1$ and R$^1$ is methyl;

1.37 Formula Q or any of 1.1-1.14 or 1.29, wherein Z is —C(O)—R$^1$ and R$^1$ is trifluoromethyl;

1.38 Formula Q or any of 1.1-1.14 or 1.29, wherein Z is —C(O)—R$^1$ and R$^1$ is —OH;

1.39 Formula Q or any of 1.1-1.14 or 1.29, wherein Z is —C(O)—R$^1$ and R$^1$ is —OC$_{1-6}$alkyl (e.g., —OCH$_3$);

1.40 Formula Q or any of 1.1-1.14 or 1.29, wherein Z is —C(O)—R$^1$ and R$^1$ is —OCH$_3$;

1.41 Formula Q or any of 1.1-1.14, wherein Z is —N(R$^2$)(R$^3$);

1.42 Formula Q or any of 1.1-1.14 or 1.32, wherein Z is —N(R$^2$)(R$^3$), wherein R$^2$ and R$^3$ are methyl;

1.43 Formula Q or any of 1.1-1.42 wherein R$^4$ and R$^5$ are independently H, C$_{1-6}$alky or aryl (e.g., phenyl) optionally substituted with one or more halo (e.g., fluorophenyl, e.g., 4-fluorophenyl), hydroxy (e.g., hydroxyphenyl, e.g., 4-hydroxyphenyl or 2-hydroxyphenyl) or C$_{1-6}$alkoxy;

1.44 Formula Q or any of 1.1-1.42 wherein either R$^4$ or R$^5$ is H;

1.45 Formula Q or any of 1.1-1.42 wherein either R$^4$ or R$^5$ is aryl (e.g., phenyl) optionally substituted with one or more halo (e.g., fluorophenyl, e.g., 4-fluorophenyl), hydroxy (e.g., hydroxyphenyl, e.g., 4-hydroxyphenyl or 2-hydroxyphenyl) or C$_{1-6}$alkoxy;

1.46 Formula Q or any of 1.1-1.42 wherein either R$^4$ or R$^5$ is aryl (e.g., phenyl) optionally substituted with one or more halo (e.g., fluorophenyl, e.g., 4-fluorophenyl), hydroxy (e.g., hydroxyphenyl, e.g., 4-hydroxyphenyl or 2-hydroxyphenyl) or C$_{1-6}$alkoxy;

1.47 Formula Q or any of 1.1-1.42 wherein either R$^4$ or R$^5$ is phenyl;

1.48 Formula Q or any of 1.1-1.42 wherein either R$^4$ or R$^5$ is phenyl substituted with fluoro (e.g., 4-fluorophenyl);

1.49 Formula Q or any of 1.1-1.42 wherein either R$^4$ or R$^5$ is phenyl substituted with hydroxy (e.g., 4-hydroxyphenyl) or C$_{1-6}$alkoxy;

1.50 any of the preceding formulae wherein —X—Y—Z is selected from 4-(5-fluoropyrid-2-yl)benzyl, 4-(6-fluoropyrid-2-yl)benzyl, 4-(3-fluoropyrid-2-yl)benzyl, 4-(6-trifluoromethylpyrid-2-yl)benzyl, 4-(4-fluoropyrid-2-yl)benzyl, 4-(5-methylpyrid-2-yl)benzyl, 4-(4-fluoropphenyl)benzyl, biphenyl-4-ylmethyl, 4-trifluoromethylphenyl, 4-(4,6-dichloropyrid-2-yl)benzyl, 4-(pyrid-2-yl)benzyl, and 4-(carboxy)benzyl, 4-(methylcarboxy)benzyl;

1.51 any of the preceding formulae wherein R$_4$ is H and R$_5$ is phenyl;

1.52 Formula Q or any of 1.1-1.51, wherein R$_4$ is H and R$_5$ is 4-fluorophenyl or 4-hydroxyphenyl;

1.53 any of the preceding formulae wherein the compound is selected from a group consisting of:

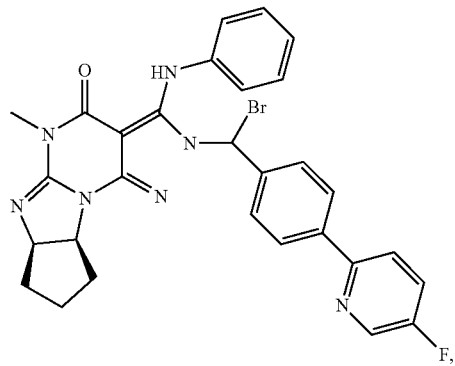

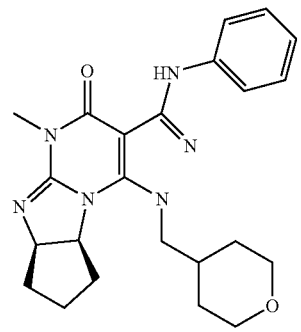

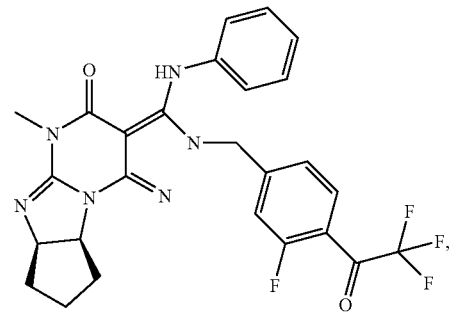

-continued
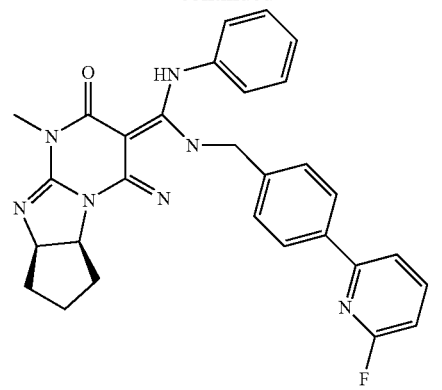
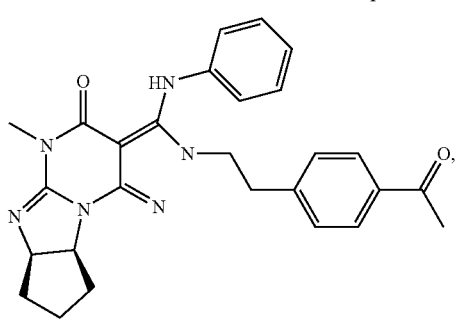
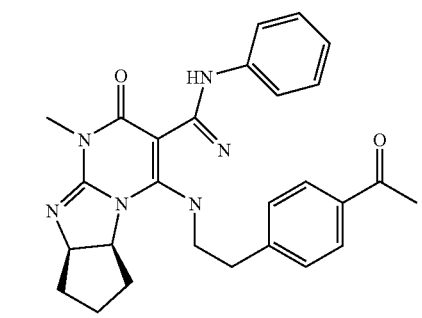
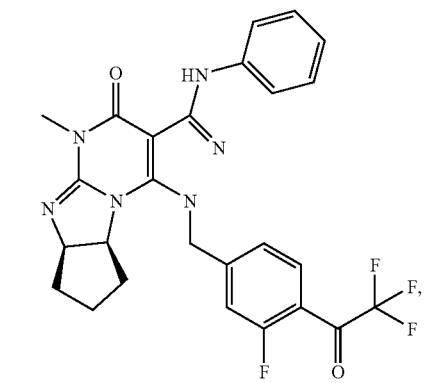
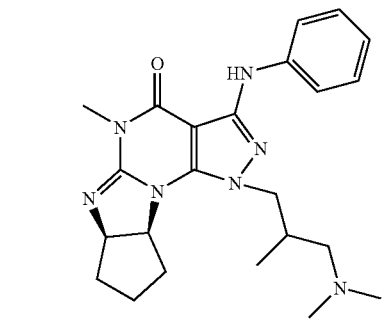
-continued
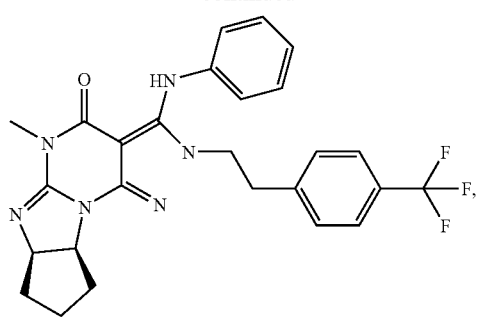
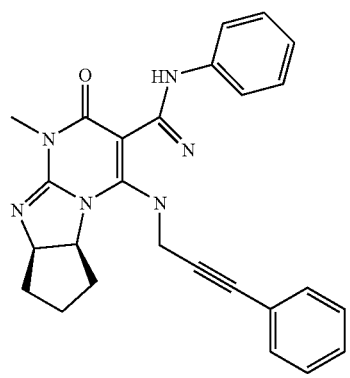
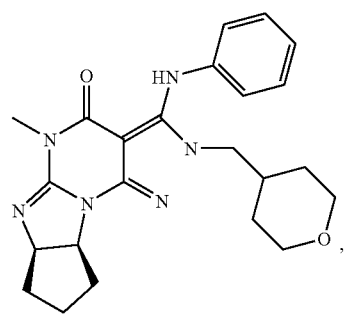
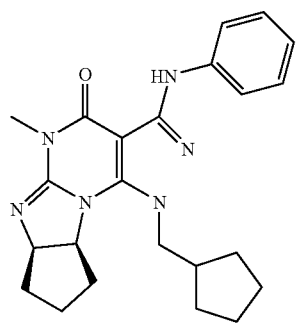
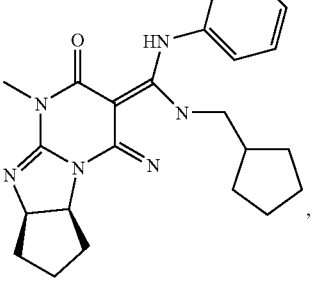

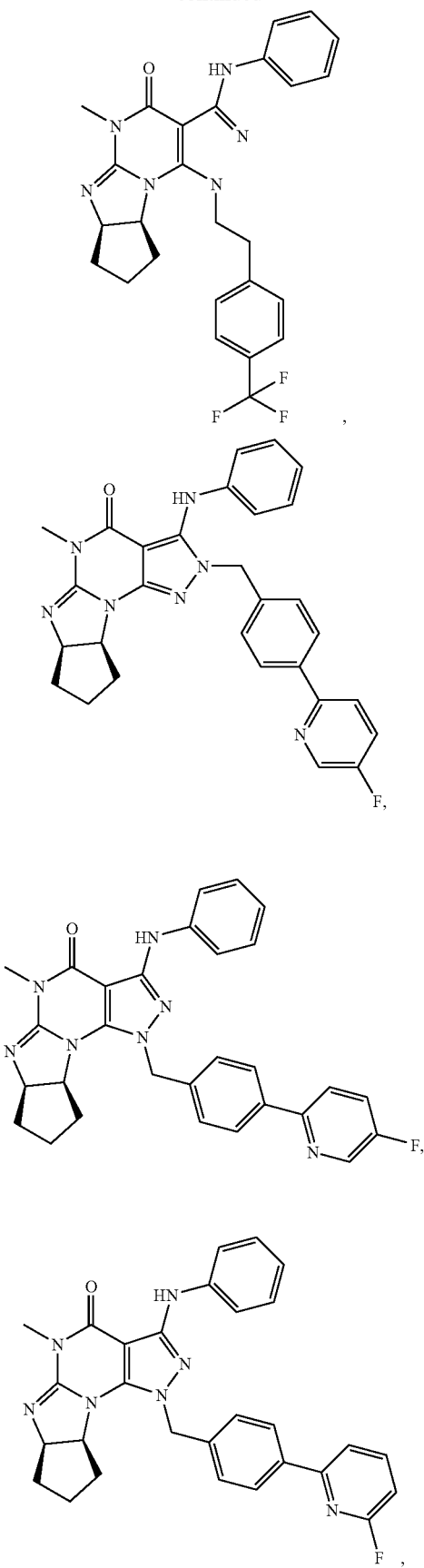
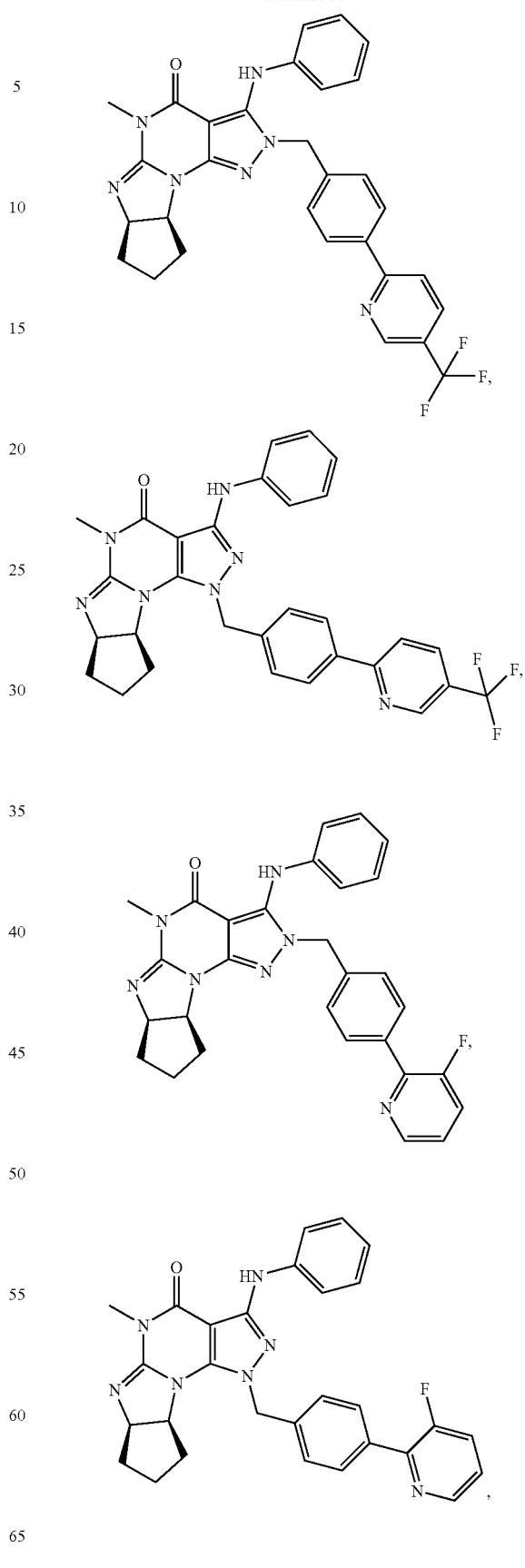

11
-continued
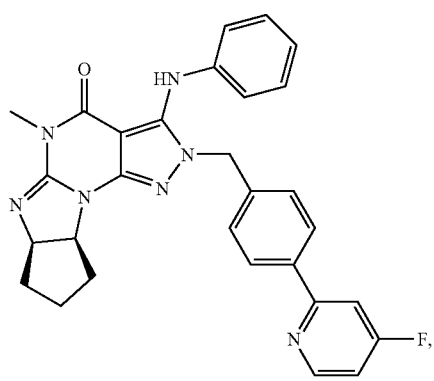
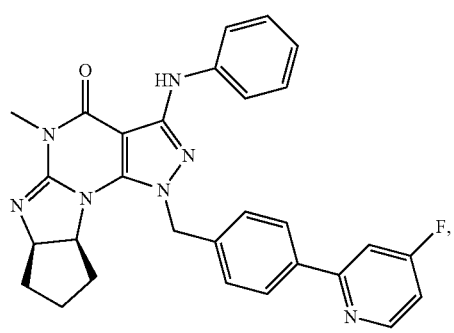
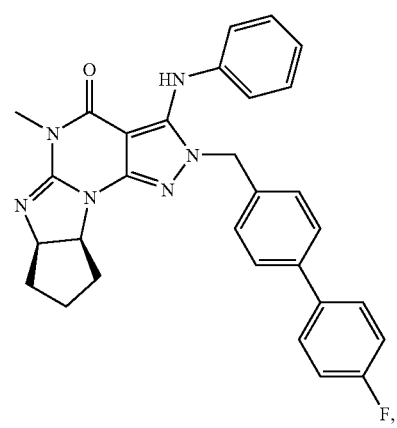
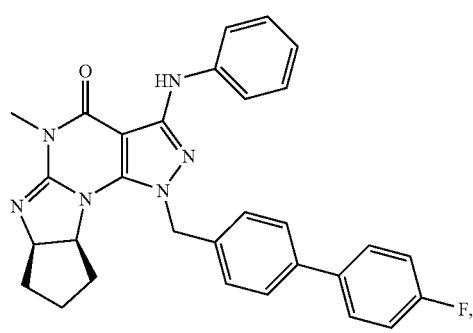
12
-continued
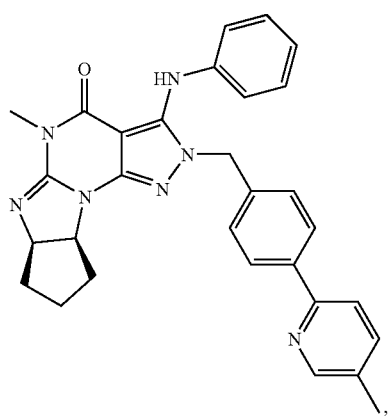
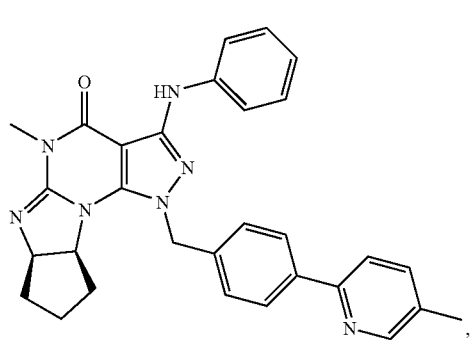
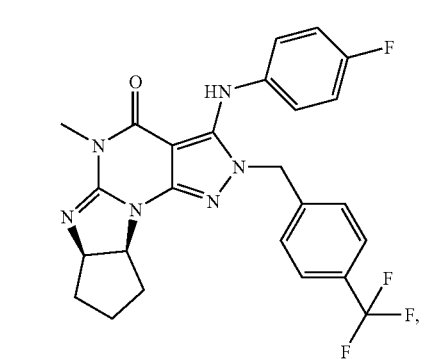
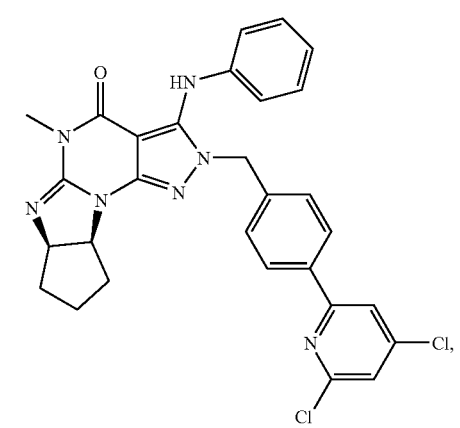

-continued
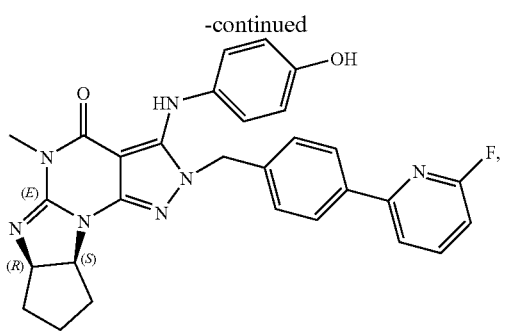
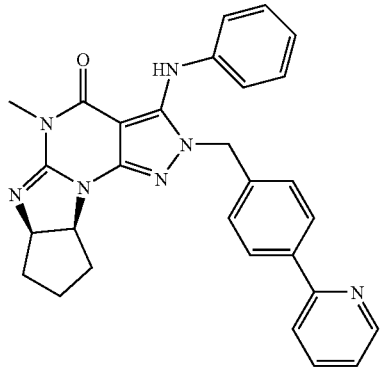
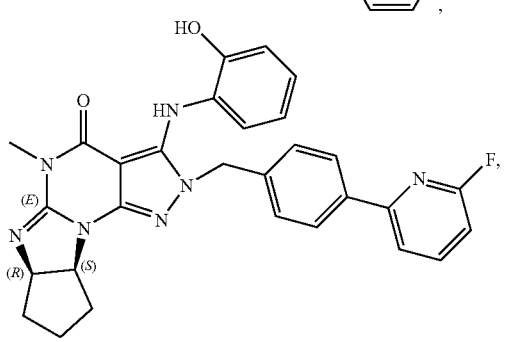
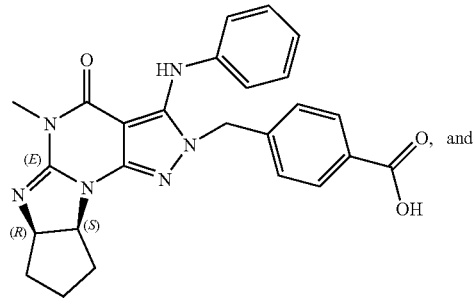
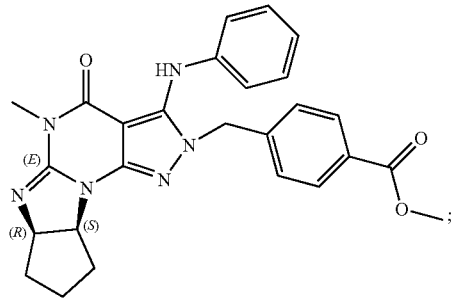
1.54 any of the preceding formulae wherein the compound is selected from a group consisting of:
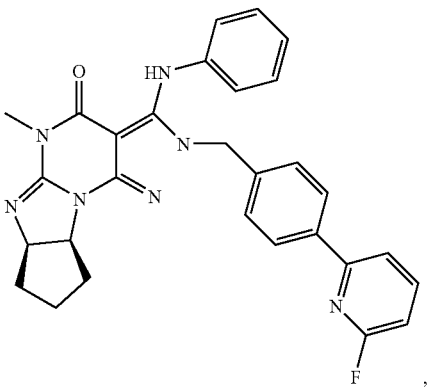
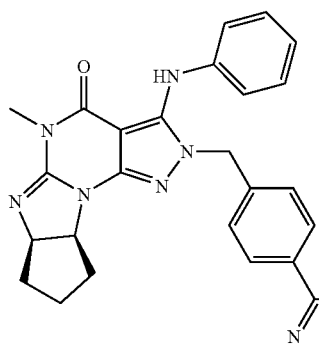
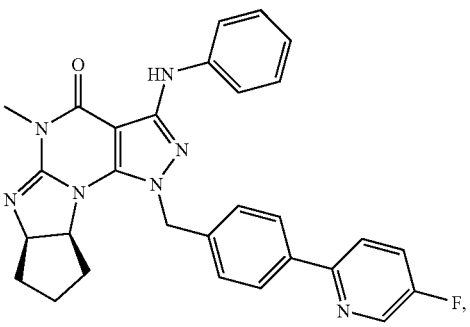
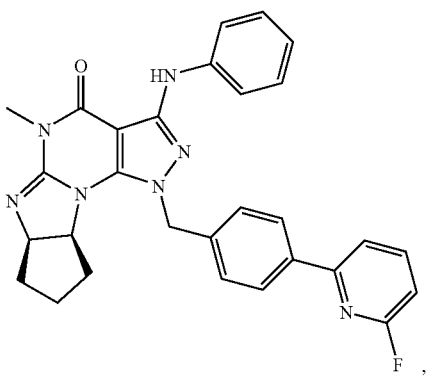

-continued
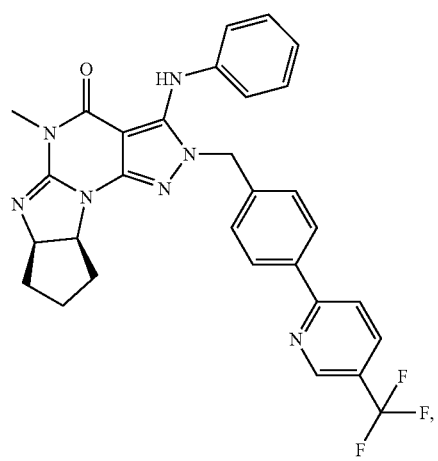
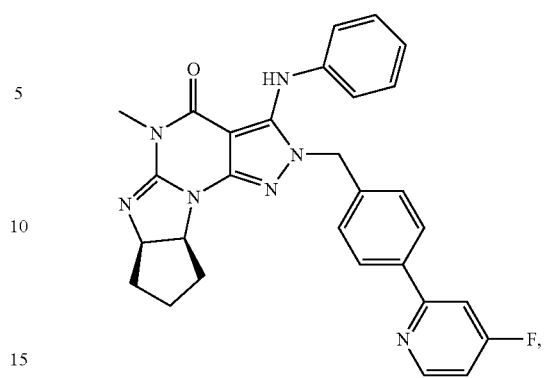
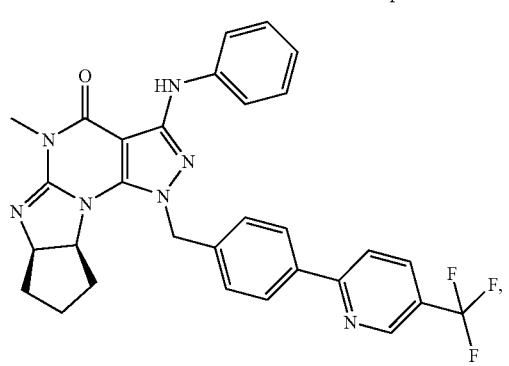
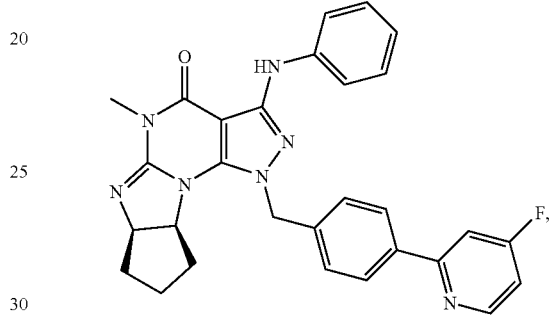
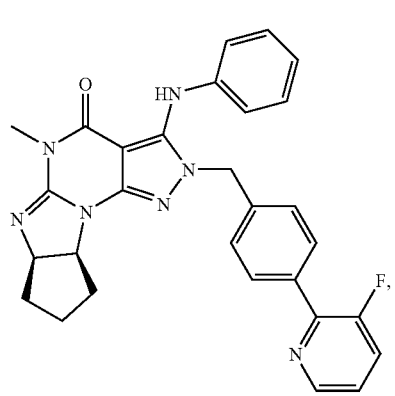
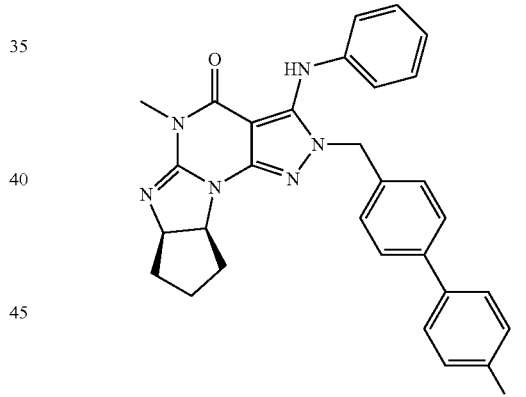
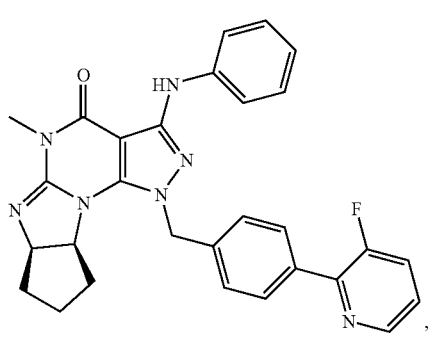
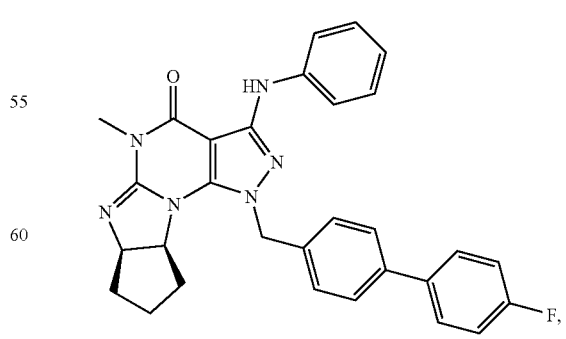

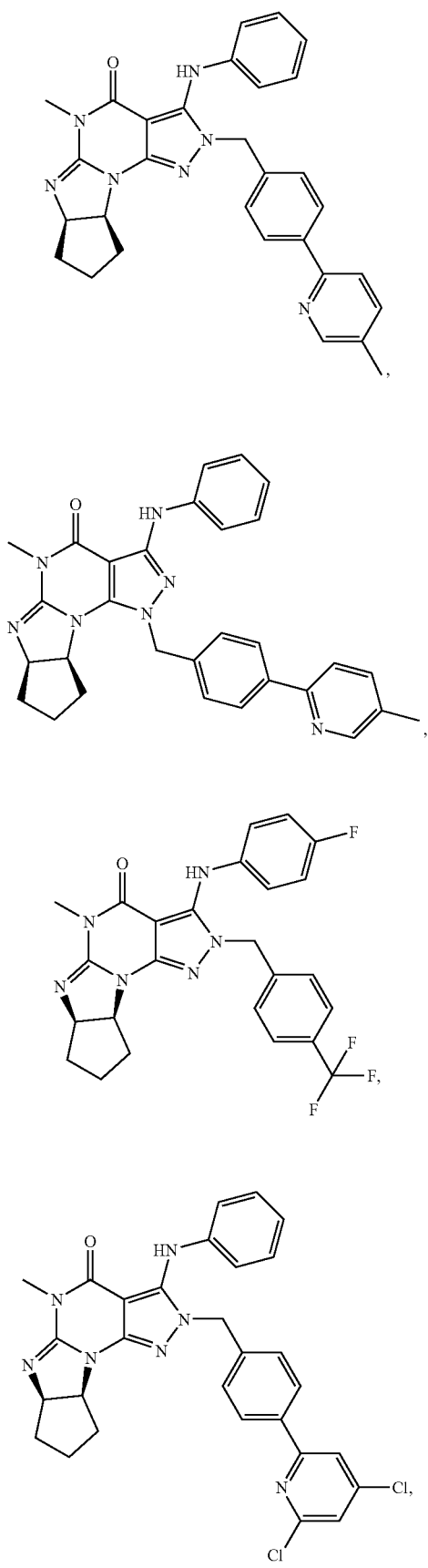
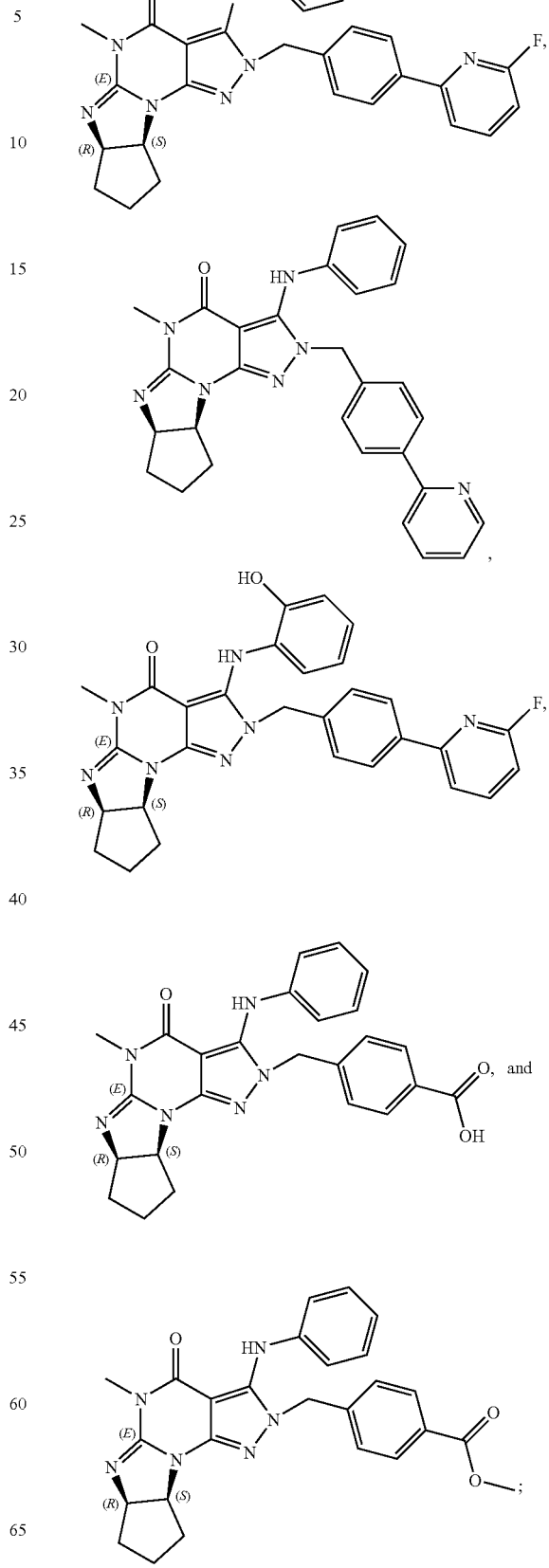

1.55 any of the preceding formulae wherein the compound is selected from a group consisting of:

-continued

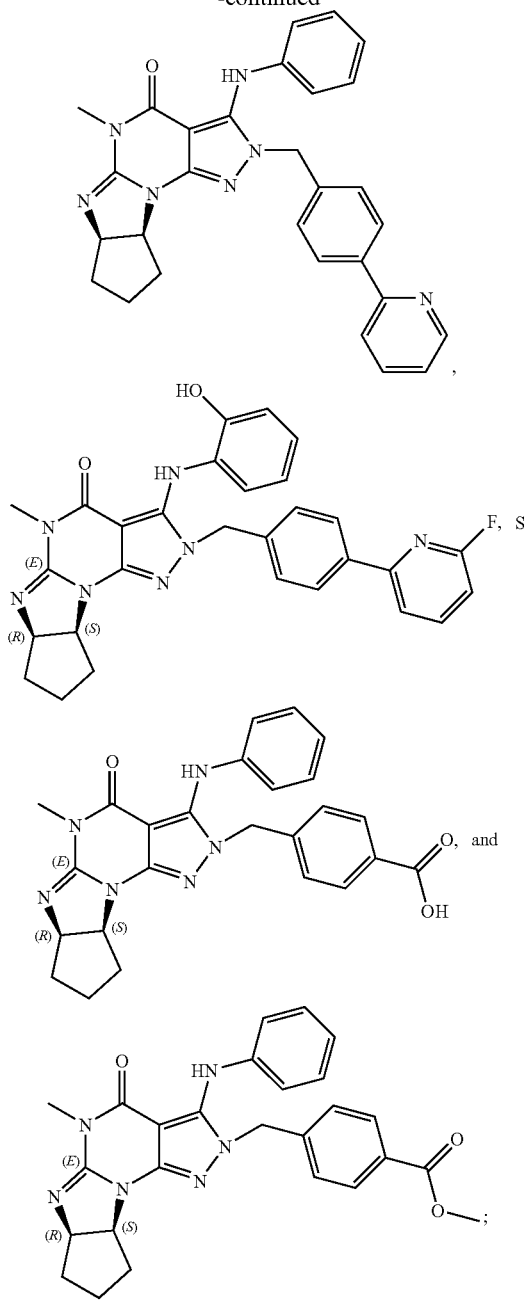

1.56 any of the preceding formulae wherein the compounds inhibit phosphodiesterase-mediated (e.g., PDE1-mediated, especially PDE1B-mediated) hydrolysis of cGMP, e.g., with an $IC_{50}$ of less than 1 μM, preferably less than 200 nM, more preferably less than 100 nM, more preferably less than 50 nM, even more preferably less than 25 nM in an immobilized-metal affinity particle reagent PDE assay, for example, as described in Example 15, in free, salt or prodrug form. In a further embodiment, the invention provides a compound of any of formulae 1.1-1.56, provided that when X is an unsubstituted methylene, Y is phenylene or heteroarylene, and Z is aryl, heteroaryl, haloalkyl or cycloalkyl, then Z is a substituted with at least one halo (e.g., fluoro, chloro, bromo) or alkyl (e.g., methyl, ethyl) group.

The invention also provides formula I

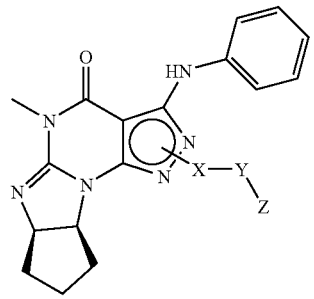

Formula I wherein
(i) X is $C_{1-4}$alkylene (e.g., methylene, ethylene or prop-2-yn-1-ylene);
(ii) Y is a single bond, alkynylene (e.g., arylene (e.g., phenylene) or heteroarylene (e.g., pyridylene);
(iii) Z is H, aryl (e.g., phenyl), heteroaryl (e.g., pyrid-2-yl), halo (e.g., F, Br, Cl), halo$C_{1-4}$alkyl (e.g., trifluoromethyl), —C(O)—$R^1$, —N($R^2$)($R^3$), or $C_{3-7}$cycloalkyl optionally containing at least one atom selected from a group consisting of N or O (e.g., cyclopentyl, cyclohexyl, tetrahydro-2H-pyran-4-yl, or morpholinyl);
(iv) $R^1$ is $C_{1-4}$alkyl, halo$C_{1-4}$alkyl;
(v) $R^2$ and $R^3$ are independently H or $C_{1-4}$alkyl,
(vi) wherein X, Y and Z are independently and optionally substituted with halo (e.g., F, Cl or Br), for example, Z is pyrid-2-yl substituted with fluoro (e.g., 6-fluoro-pyrid-2-yl), in free, salt or prodrug form, including its enantiomers, diastereoisomers and racemates, provided that when X is an unsubstituted methylene, Y is phenylene or heteroarylene, and Z is aryl, heteroaryl, haloalkyl or cycloalkyl, then Z is a substituted with at least one halo (e.g., fluoro, chloro, bromo) or alkyl (e.g., methyl, ethyl) group.

Preferably, (6aR,9aS)-3-(phenylamino)-5-6a,7,8,9,9a-hexahydro-5-methyl-cyclopent[4,5]imidazo[1,2-a]pyrazolo[4,3-e]pyrimidin-4(2H)-ones is 2-substituted e.g., —X—Y—Z is substituted on the 2-position of the pyrazolo ring of Formula I, for example:

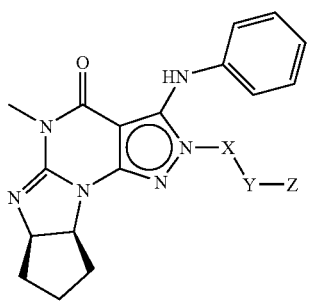

Formula II

More preferably, when Y is phenylene and Z is substituted at the para-position of the phenyl ring.

The invention further provides compounds of Formula I as follows:
1.57 Formula I, wherein X is $C_{1-4}$alkylene (e.g., methylene, ethylene or prop-2-yn-1-ylene) optionally substituted with halo;

1.58 Formula I or 1.57, wherein X is methylene or ethylene optionally substituted with halo;
1.59 Formula I, 1.57 or 1.58, wherein X is methylene optionally substituted with halo;
1.60 Formula I, 1.57, 1.58 or 1.59, wherein X is methylene substituted with bromo;
1.61 Formula I, 1.57, 1.58, 1.59 or 1.60, wherein X is ethylene;
1.62 Formula I or any of 1.57-1.61, wherein X is $C_1$ prop-2-yn-1-ylene;
1.63 Formula I or any of 1.57-1.62, wherein Y is a single bond, arylene (e.g., phenylene) or heteroarylene (e.g., pyridylene) optionally substituted with halo;
1.64 Formula I or any of 1.57-1.63, wherein Y is arylene (e.g., phenylene) optionally substituted with halo;
1.65 Formula I or any of 1.57-1.64 wherein Y is phenylene optionally substituted with fluoro at the 3 or 5-position of the phenylene ring;
1.66 Formula I or any of 1.57-1.65, wherein Y is phenylene;
1.67 Formula I or any of 1.57-1.63, wherein Y is heteroarylene (e.g., pyridylene) optionally substituted with halo;
1.68 Formula I or any of 1.57-1.63, wherein Y is a single bond;
1.69 Formula I or any of 1.57-1.63, wherein Y is heteroaryl (e.g., pyrid-2-yl);
1.70 Formula I or any of 1.57-1.69, wherein Z is H, aryl (e.g., phenyl), heteroaryl (e.g., pyrid-2-yl), halo (e.g., F, Br, Cl), halo$C_{1-4}$alkyl (e.g., trifluoromethyl), —C(O)—$R^1$, —N($R^2$)($R^3$), or $C_{3-7}$cycloalkyl optionally containing at least one atom selected from a group consisting of N or O (e.g., cyclopentyl, cyclohexyl, tetrahydro-2H-pyran-4-yl, or morpholinyl), optionally substituted with halo;
1.71 Formula I or any of 1.57-1.70, wherein Z is $C_{3-7}$cycloalkyl optionally containing at least one atom selected from a group consisting of N or O (e.g., cyclopentyl, cyclohexyl, tetrahydro-2H-pyran-4-yl, morpholinyl);
1.72 Formula I or any of 1.57-1.71, wherein Z is cyclopentyl;
1.73 Formula I or any of 1.57-1.71, wherein Z is tetrahydro-2H-pyran-4-yl;
1.74 Formula I or any of 1.57-1.70, wherein Z is heteroaryl (e.g., pyrid-2-yl) optionally substituted with halo;
1.75 Formula I or any of 1.57-1.70 or 1.74, wherein Z is pyrid-2-yl;
1.76 Formula I or any of 1.57-1.70 or 1.74, wherein Z is 5-fluoro-pyrid-2-yl or 6-fluoro-pyrid-2-yl;
1.77 Formula I or any of 1.57-1.70, wherein Z is halo$C_{1-4}$ alkyl (e.g., trifluoromethyl);
1.78 Formula I or any of 1.57-1.70 or 1.77, wherein Z is trifluoromethyl;
1.79 Formula I or any of 1.57-1.70, wherein Z is —C(O)—$R^1$ and $R^1$ is $C_{1-4}$alky (e.g., methyl) or halo$C_{1-4}$alkyl (e.g., trifluoromethyl);
1.80 Formula I or any of 1.57-1.70 or 1.79, wherein Z is —C(O)—$R^1$ and $R^1$ is methyl;
1.81 Formula I or any of 1.57-1.70 or 1.79, wherein Z is —C(O)—$R^1$ and $R^1$ is trifluoromethyl;
1.82 Formula I or any of 1.57-1.70, wherein Z is aryl (e.g., phenyl) optionally substituted with halo (e.g., fluoro);
1.83 Formula I or any of 1.57-1.70 or 1.82, wherein Z is phenyl;
1.84 Formula I or any of 1.57-1.70, wherein Z is —N($R^2$)($R^3$);
1.85 Formula I or any of 1.57-1.70 or 1.84, wherein Z is —N($R^2$)($R^3$), wherein $R^2$ and $R^3$ are methyl;
1.86 any of the preceding formulae wherein the compound is selected from a group consisting of:

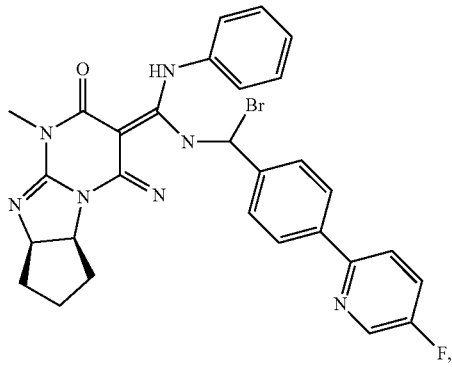

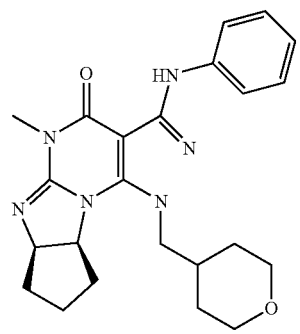

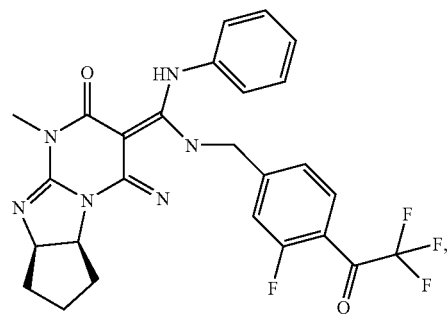

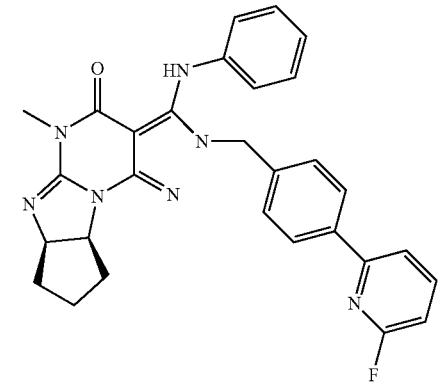

27
-continued
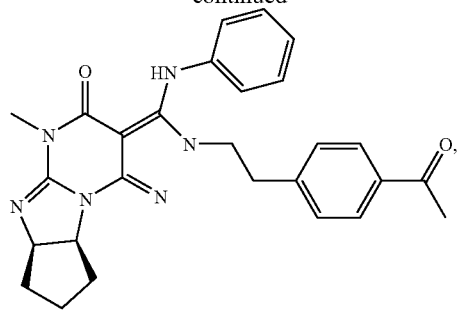
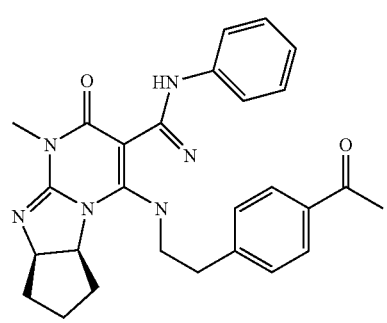
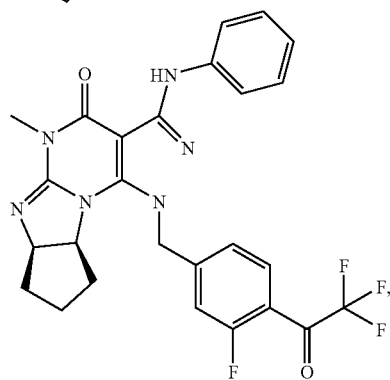
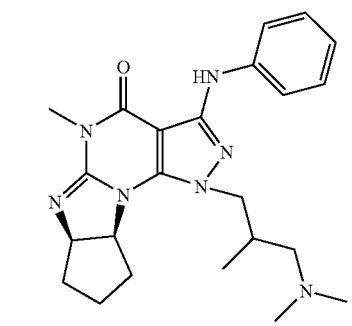
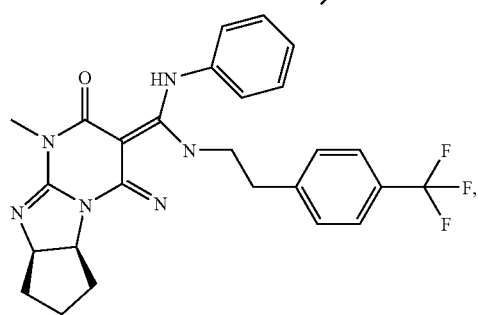
28
-continued
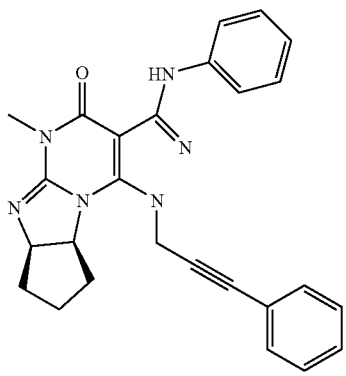
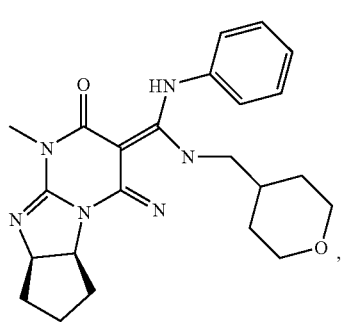
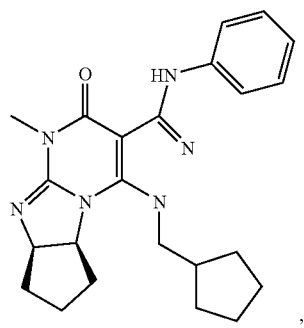
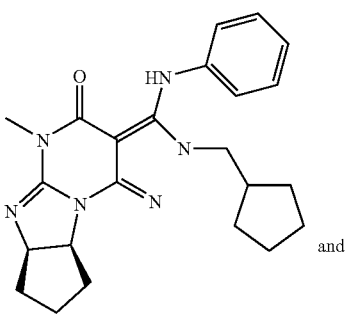
and

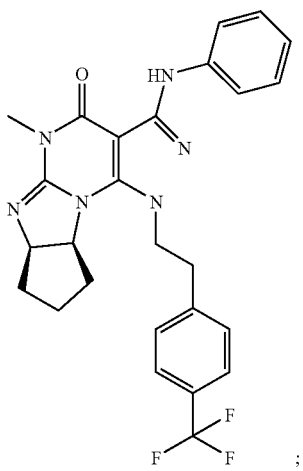

1.87 any of the preceding formulae wherein the compounds inhibit phosphodiesterase-mediated (e.g., PDE1-mediated, especially PDE1B-mediated) hydrolysis of cGMP, e.g., with an $IC_{50}$ of less than 1 μM, preferably less than 25 nM in an immobilized-metal affinity particle reagent PDE assay, for example, as described in Example 15, in free, salt or prodrug form, including its enantiomers, diastereoisomers and racemates, provided that when X is an unsubstituted methylene, Y is phenylene or heteroarylene, and Z is aryl, heteroaryl, haloalkyl or cycloalkyl, then Z is a substituted with at least one halo (e.g., fluoro, chloro, bromo) or alkyl (e.g., methyl, ethyl) group.

Preferably, the compound of the present invention is:

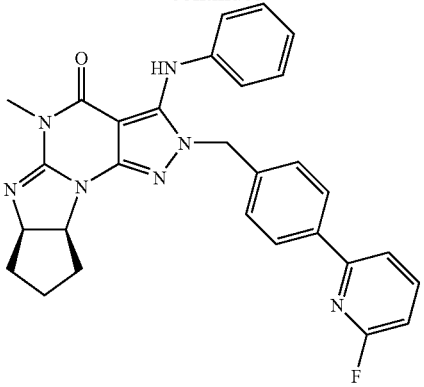

in free, salt or prodrug form.

In another aspect of the invention, there is provided a Compound of Formula (X):

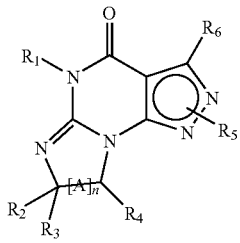

Formula (X)

wherein
(i) $R_1$ is H or $C_{1-6}$ alkyl (e.g., methyl);
(ii) $R_4$ is H or $C_{1-6}$ alkyl and $R_2$ and $R_3$ are, independently, H or $C_{1-6}$alkyl optionally substituted with halo or hydroxyl (e.g., $R_2$ and $R_3$ are both methyl, or $R_2$ is H and $R_3$ is ethyl, isopropyl or hydroxyethyl), aryl, heteroaryl, (optionally hetero)arylalkoxy, or (optionally hetero) aryl$C_{1-6}$alkyl;
or
$R_2$ is H and $R_3$ and $R_4$ together form a di-, tri- or tetramethylene bridge (pref. wherein the $R_3$ and $R_4$ together have the cis configuration, e.g., where the carbons carrying $R_3$ and $R_4$ have the R and S configurations, respectively);
(iii) $R_5$ is a substituted heteroaryl$C_{1-6}$alkyl, e.g., substituted with $C_{1-6}$haloalkyl;
$R_5$ is -D-E-F, wherein:
D is $C_{1-6}$alkylene (e.g., methylene, ethylene or prop-2-yn-1-ylene);
E is a single bond, alkynylene (e.g., —C≡C—), arylene (e.g., phenylene) or heteroarylene (e.g., pyridylene);
F is H, aryl (e.g., phenyl), heteroaryl (e.g., pyridyl, e.g., pyrid-2-yl), halo (e.g., F, Br, Cl), halo$C_{1-6}$alkyl (e.g., trifluoromethyl), —C(O)—$R_{15}$, —N($R_{16}$) ($R_{17}$), or $C_{3-7}$cycloalkyl optionally containing at least one atom selected from a group consisting of N or O (e.g., cyclopentyl, cyclohexyl, tetrahydro-2H-pyran-4-yl, or morpholinyl);
wherein D, E and F are independently and optionally substituted with one or more halo (e.g., F, Cl or Br), $C_{1-6}$alkyl (e.g., methyl), halo$C_{1-6}$alkyl (e.g., trifluoromethyl), for example, Z is heteroaryl, e.g., pyridyl substituted with one or more halo (e.g., 6-fluoropyrid-2-yl, 5-fluoropyrid-2-yl, 6-fluoropyrid-2-yl, 3-fluoropyrid-2-yl, 4-fluoropyrid-2-yl, 4,6-dichloropyrid-2-yl), haloC$_{1-6}$alkyl (e.g., 5-trifluoromethylpyrid-2-yl) or C$_{1-6}$alkyl (e.g., 5-methylpyrid-2-yl), or Z is aryl, e.g., phenyl, substituted with one or more halo (e.g., 4-fluorophenyl);
or
R$_5$ is attached to one of the nitrogens on the pyrazolo portion of Formula (X) and is a moiety of Formula A

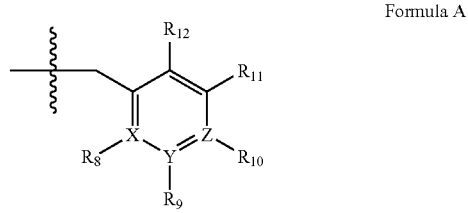

Formula A wherein X, Y and Z are, independently, N or C, and R$_8$, R$_9$, R$_{11}$ and R$_{12}$ are independently H or halogen (e.g., Cl or F), and R$_{10}$ is halogen, alkyl, cycloalkyl, haloalkyl (e.g., trifluoromethyl), aryl (e.g., phenyl), heteroaryl (e.g., pyridyl (for example pyrid-2-yl), or thiadiazolyl (e.g., 1,2,3-thiadiazol-4-yl)), diazolyl, triazolyl, tetrazolyl, arylcarbonyl (e.g., benzoyl), alkylsulfonyl (e.g., methylsulfonyl), heteroarylcarbonyl, or alkoxycarbonyl; provided that when X, Y, or Z is nitrogen, R$_8$, R$_9$, or R$_{10}$, respectively, is not present; and (iv) R$_6$ is H, alkyl, aryl, heteroaryl, arylalkyl (e.g., benzyl), arylamino (e.g., phenylamino), heterarylamino, N,N-dialkylamino, N,N-diarylamino, or N-aryl-N-(arylakyl) amino (e.g., N-phenyl-N-(1,1'-biphen-4-ylmethyl) amino);
or
R$_6$ is —N(R$_{18}$)(R$_{19}$) wherein R$_{18}$ and R$_{19}$ are independently H, C$_{1-6}$alky or aryl (e.g., phenyl) wherein said aryl is optionally substituted with one or more halo (e.g., fluorophenyl, e.g., 4-fluorophenyl) or hydroxy (e.g., hydroxyphenyl, e.g., 4-hydroxyphenyl or 2-hydroxyphenyl);

(v) n=0 or 1;
(vi) when n=1, A is —C(R$_{13}$R$_{14}$)—;
(vii) wherein R$_{13}$ and R$_{14}$, are, independently, H or C$_{1-6}$ alkyl, aryl, heteroaryl, (optionally hetero)arylalkoxy or (optionally hetero)arylalkyl;
(viii) R$_{15}$ is C$_{1-6}$alkyl, haloC$_{1-6}$alkyl, —OH or —OC$_{1-6}$alkyl (e.g., —OCH$_3$);
(ix) R$_{16}$ and R$_{17}$ are independently H or C$_{1-6}$alkyl;
in free, salt or prodrug form.

In a further embodiment of this aspect of the invention, the Compound of Formula (X) is:

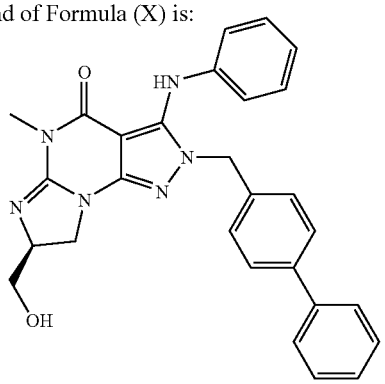

in free, salt or prodrug from.

More preferably, the Compound of the Invention is selected from formula 1.54, in free, salt or prodrug form. More preferably, the Compound of the Invention is selected from formula 1.55, in free, salt or prodrug form.

If not otherwise specified or clear from context, the following terms herein have the following meanings:

(a) "Alkyl" as used herein is a saturated or unsaturated hydrocarbon moiety, preferably saturated, preferably having one to six carbon atoms, which may be linear or branched, and may be optionally mono-, di- or tri-substituted, e.g., with halogen (e.g., chloro or fluoro), hydroxy, or carboxy.

(b) "Cycloalkyl" as used herein is a saturated or unsaturated nonaromatic hydrocarbon moiety, preferably saturated, preferably comprising three to nine carbon atoms, at least some of which form a nonaromatic mono- or bicyclic, or bridged cyclic structure, and which may be optionally substituted, e.g., with halogen (e.g., chloro or fluoro), hydroxy, or carboxy.

(c) "Aryl" as used herein is a mono or bicyclic aromatic hydrocarbon, preferably phenyl, optionally substituted, e.g., with alkyl (e.g., methyl), halogen (e.g., chloro or fluoro), haloalkyl (e.g., trifluoromethyl), hydroxy, carboxy, or an additional aryl or heteroaryl (e.g., biphenyl or pyridylphenyl).

(d) "Heteroaryl" as used herein is an aromatic moiety wherein one or more of the atoms making up the aromatic ring is sulfur or nitrogen rather than carbon, e.g., pyridyl or thiadiazolyl, which may be optionally substituted, e.g., with alkyl, halogen, haloalkyl, hydroxy or carboxy.

(e) For ease of reference, the atoms on the pyrazolo-pyrimidine core of the Compounds of the Invention are numbered in accordance with the numbering depicted in Formula I, unless otherwise noted.

(f) Wherein Y is phenylene, the numbering is as follows:

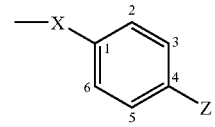

(g) It is intended that wherein the substituents end in "ene", for example, alkylene, phenylene or arylalkylene, said substitutents are intended to bridge or be connected to two other substituents. Therefore, methylene is intended to be —CH$_2$— and phenylene intended to be —C$_6$H$_4$— and arylalkylene is intended to be —C$_6$H$_4$—CH$_2$— or —CH$_2$—C$_6$H$_4$—.

Compounds of the Invention may exist in free or salt form, e.g., as acid addition salts. In this specification unless otherwise indicated, language such as "Compounds of the Invention" is to be understood as embracing all the novel compounds disclosed herein, e.g., 1- or 2-substituted (6aR*, 9aS*)-3-(phenylamino)-5-6a,7,8,9,9a-hexahydro-5-methyl-cyclopent[4,5]imidazo[1,2-a]pyrazolo[4,3-e]pyrimidin-4 (1H or 2H)-one compounds, preferably 1- or 2-substituted (6aR,9aS) (phenylamino)-5-6a,7,8,9,9a-hexahydro-5-methyl-cyclopent[4,5]imidazo[1,2-a]pyrazolo[4,3-e]pyrimidin-4(1H or 2H)-one, the Compounds of Formula Q, e.g., any of 1.1-1.56, Compound of Formula (X), or Formula I, e.g., any of 1.57-1.87, any of these compounds in any form, for example free or acid addition salt form, or where the compounds contain acidic substituents, in base addition salt form.

The Compounds of the Invention are intended for use as pharmaceuticals, therefore pharmaceutically acceptable salts are preferred. Salts which are unsuitable for pharmaceutical uses may be useful, for example, for the isolation or purification of free Compounds of the Invention or their pharmaceutically acceptable salts, are therefore also included.

Compounds of the Invention may in some cases also exist in prodrug form. A prodrug form is compound which converts in the body to a Compound of the Invention. For example when the Compounds of the Invention contain hydroxy or carboxy substituents, these substituents may form physiologically hydrolysable and acceptable esters. As used herein, "physiologically hydrolysable and acceptable ester" means esters of Compounds of the Invention which are hydrolysable under physiological conditions to yield acids (in the case of Compounds of the Invention which have hydroxy substituents) or alcohols (in the case of Compounds of the Invention which have carboxy substituents) which are themselves physiologically tolerable at doses to be administered. As will be appreciated the term thus embraces conventional pharmaceutical prodrug forms.

The invention also provides methods of making the Compounds of the Invention and methods of using the Compounds of the Invention for treatment of diseases and disorders as set forth below (especially treatment of diseases characterized by reduced dopamine D1 receptor signaling activity, such as Parkinson's disease, Tourette's Syndrome, Autism, fragile X syndrome, ADHD, restless leg syndrome, depression, cognitive impairment of schizophrenia, narcolepsy and diseases that may be alleviated by the enhancement of progesterone-signaling such as female sexual dysfunction).

DETAILED DESCRIPTION OF THE INVENTION

Methods of Making Compounds of the Invention

The compounds of the Invention, e.g., a (6aR*,9aS*)-3-(phenylamino)-5-6a,7,8,9,9a-hexahydro-5-methyl-cyclopent[4,5]imidazo[1,2-a]pyrazolo[4,3-e]pyrimidin-4(1H or 2H)-one compounds, preferably 1- or 2-substituted (6aR, 9aS) (phenylamino)-5-6a,7,8,9,9a-hexahydro-5-methyl-cyclopent[4,5]imidazo[1,2-a]pyrazolo[4,3-e]pyrimidin-4(1H or 2H)-one, a Compound of formula Q or I, e.g., any of 1.1-0.56 or 1.5701.87, or a Compound of Formula (X), and their pharmaceutically acceptable salts may be made using the methods as described and exemplified herein and by methods similar thereto and by methods known in the chemical art. Such methods include, but not limited to, those described below. If not commercially available, starting materials for these processes may be made by procedures, which are selected from the chemical art using techniques which are similar or analogous to the synthesis of known compounds. All references cited herein are hereby incorporated in their entirety by reference.

The Compounds of the Invention include their enantiomers, diastereoisomers and racemates, as well as their polymorphs, hydrates, solvates and complexes. Some individual compounds within the scope of this invention may contain double bonds. Representations of double bonds in this invention are meant to include both the E and the Z isomer of the double bond. In addition, some compounds within the scope of this invention may contain one or more asymmetric centers. This invention includes the use of any of the optically pure stereoisomers as well as any combination of stereoisomers.

Melting points are uncorrected and (dec) indicates decomposition. Temperature are given in degrees Celsius (° C.); unless otherwise stated, operations are carried out at room or ambient temperature, that is, at a temperature in the range of 18-25° C. Chromatography means flash chromatography on silica gel; thin layer chromatography (TLC) is carried out on silica gel plates. NMR data is in the delta values of major diagnostic protons, given in parts per million (ppm) relative to tetramethylsilane (TMS) as an internal standard. Conventional abbreviations for signal shape are used. Coupling constants (J) are given in Hz. For mass spectra (MS), the lowest mass major ion is reported for molecules where isotope splitting results in multiple mass spectral peaks Solvent mixture compositions are given as volume percentages or volume ratios. In cases where the NMR spectra are complex, only diagnostic signals are reported.

Terms and abbreviations:
BuLi=n-butyllithium
Bu$^t$OH=tert-butyl alcohol,
CAN=ammonium cerium (IV) nitrate,
DIPEA=diisopropylethylamine,
DMF=N,N-dimethylforamide,
DMSO=dimethyl sulfoxide,
Et$_2$O=diethyl ether,
EtOAc=ethyl acetate,
equiv.=equivalent(s),
h=hour(s),
HPLC=high performance liquid chromatography,
LDA=lithium diisopropylamide
MeOH=methanol,
NBS=N-bromosuccinimide
NCS=N-chlorosuccinimide
NaHCO$_3$=sodium bicarbonate,
NH$_4$OH=ammonium hydroxide,
Pd$_2$(dba)$_3$=tris[dibenzylideneacetone]dipalladium(0)
PMB=p-methoxybenzyl,
POCl$_3$=phosphorous oxychloride,
SOCl$_2$=thionyl chloride,
TFA=trifluoroacetic acid,
THF=tetrahedrofuran.

The synthetic methods in this invention are illustrated below. The significances for the R groups are as set forth above for formula I unless otherwise indicated.

In an aspect of the invention, intermediate compounds of formula IIb can be synthesized by reacting a compound of formula IIa with a dicarboxylic acid, acetic anhydride and acetic acid mixing with heat for about 3 hours and then cooled:

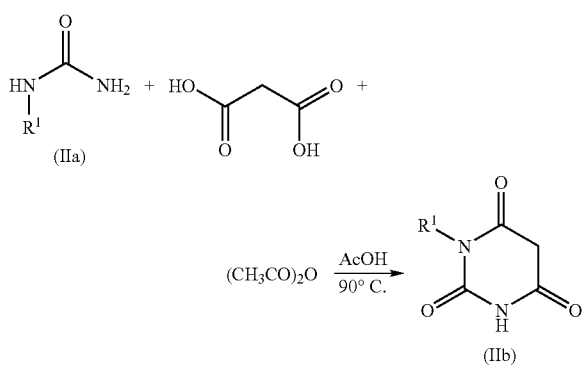

wherein R$^1$ is methyl.

Intermediate IIc can be prepared by for example reacting a compound of IIb with for example a chlorinating compound such as POCl₃, sometimes with small amounts of water and heated for about 4 hours and then cooled

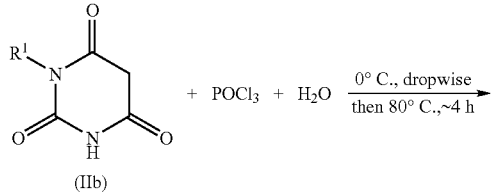

(IIb)

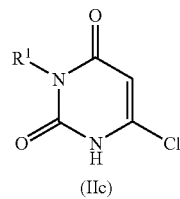

(IIc)

Intermediate IId may be formed by reacting a compound of IIc with for example a P¹-L in a solvent such as DMF and a base such as K₂CO₃ at room temperature or with heating:

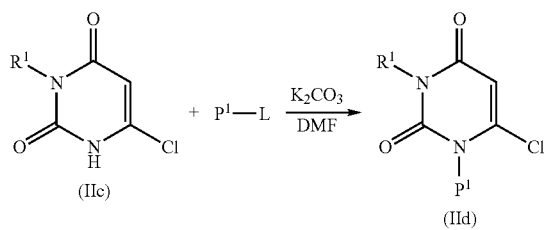

wherein P¹ is a protective group [e.g., p-methoxybenzyl group (PMB)]; L is a leaving group such as a halogen, mesylate, or tosylate.

Intermediate IIe may be prepared by reacting a compound of IId with hydrazine or hydrazine hydrate in a solvent such as methanol and refluxed for about 4 hours and then cooled:

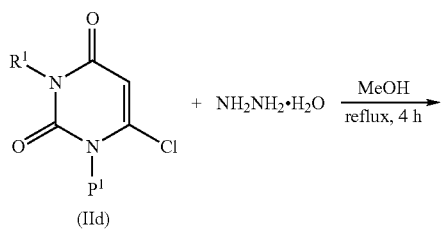

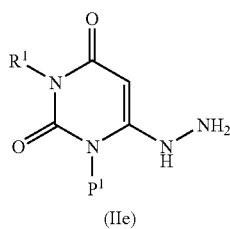

(IIe)

Intermediate IIf can be synthesized by reacting a compound of IIe with hydrazine or hydrazine hydrate in a solvent such as methoxyethanol and refluxed for about 30 min and then cooled:

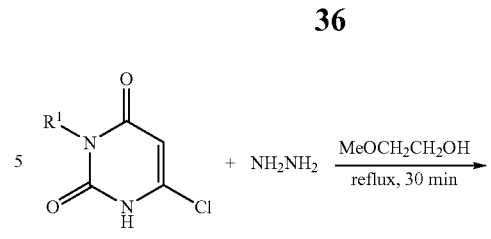

Intermediate IIg (wherein R¹³ phenyl), can be synthesized by reacting a compound of IIe with for example an aryl isothiocyanate or isocyanate in a solvent such as DMF and heated at 110° C. for about 2 days and then cooled:

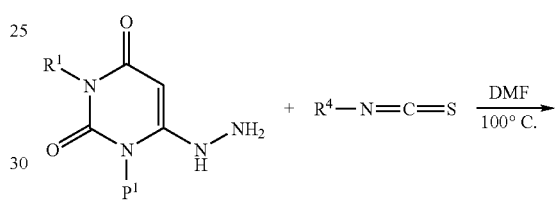

Intermediate IIh may be synthesized from a compound of IIg by removing the protective group P¹ with an appropriate method. For example, if P¹ is a p-methoxybenzyl group, then it can be removed with AlCl₃ at room temperature or with TFA under heated conditions.

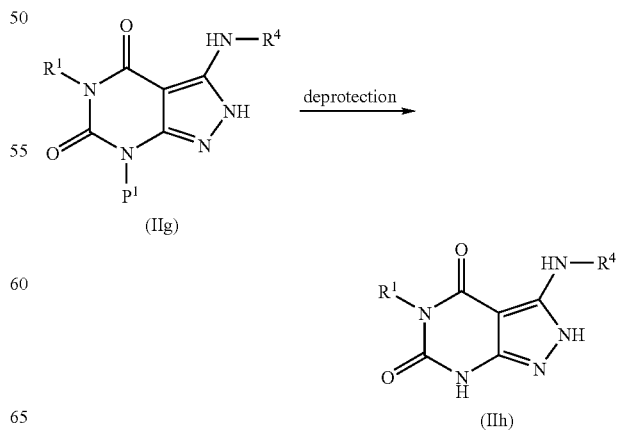

Intermediate IIh may also be prepared directly from a compound of IIf using the similar methods, but the yields are relatively low.

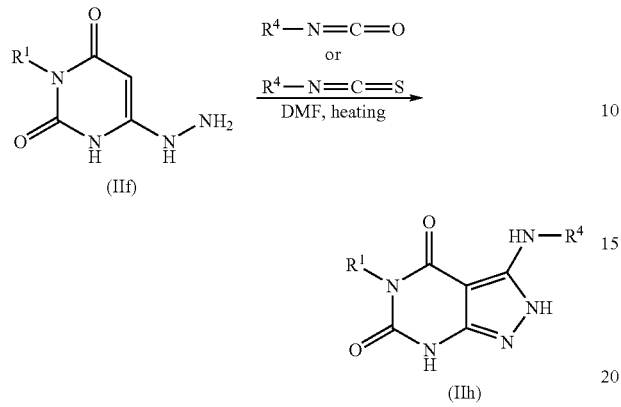

Intermediate II-I can be prepared by for example reacting a compound of IIh with for example a chlorinating compound such as POCl$_3$. The reaction may be carried out at atmospheric pressure and refluxed for about 2 days, or heated at 150–200° C. for about 10 min in a sealed vial with a microwave instrument.

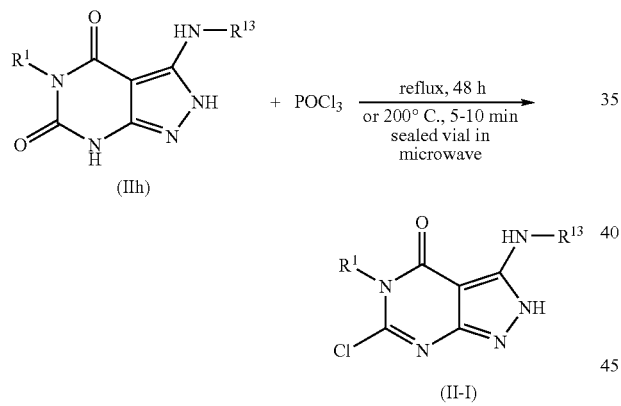

Intermediate IIJ can be prepared by reacting a compound of II-I with an amino alcohol, e.g., (1R,2R)-1-amino-2-cyclopentanol, in a solvent such as DMF. The reaction may be heated overnight and then cooled. The reaction mixture may be purified by chromatography to obtain compound IIJ:

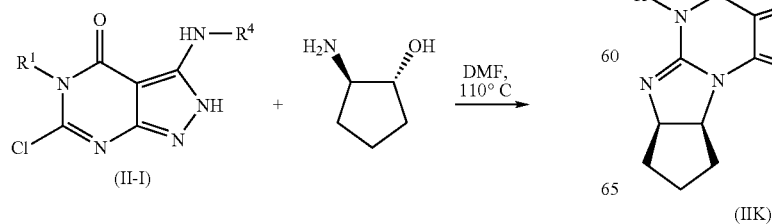

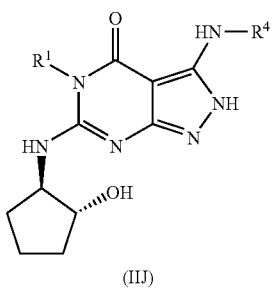

Intermediate IIK can be formed by reacting a compound of IIJ with for example a dehydrating/halogenating agent such as SOCl$_2$ in a solvent such as CH$_2$Cl$_2$ at room temperature overnight or heated at 35° C. for about 4 hours, and then cooled to obtain cyclized compound (IIK).

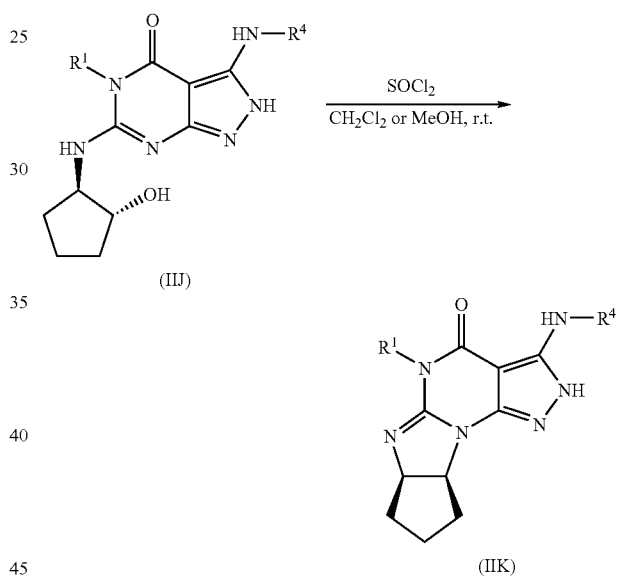

Compound Ia and Ib may be formed by reacting a compound of IIk with for example a Z—Y—X-L in a solvent such as DMF and a base such as K$_2$CO$_3$ at room temperature or with heating:

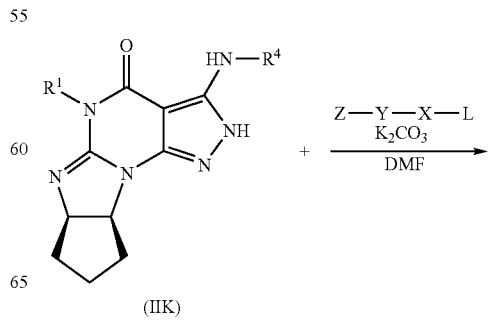

-continued

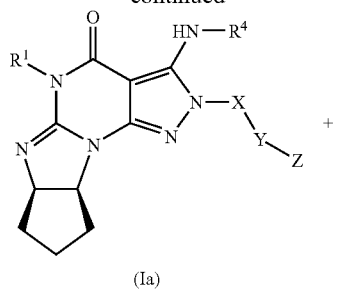

(Ia)

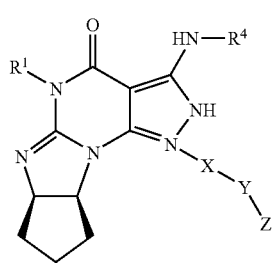

(Ib)

wherein all the substitutents are as defined previously; L is a leaving group such as a halogen, mesylate, or tosylate.

X—Y—Z may also be introduced earlier by for example reacting IIg with Z—Y—X-L and then perform similar procedure as described above to form compound Ia and Ib, as long as Z—Y—X will not be cleaved off in the $P^1$ deprotection step.

The third synthetic route is also developed for the preparation of Compound Ia.

Intermediate IVa may be formed by for example reacting a compound of IIe with $POCl_3$ and DMF:

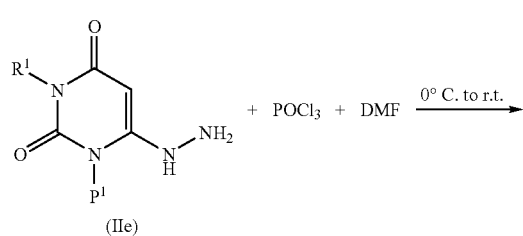

(IIe)

wherein $R^1$ is methyl.

Intermediate IVb may be formed by reacting a compound of IVa with for example a Z—Y—X-L in a solvent such as DMF and a base such as $K_2CO_3$ at room temperature or with heating:

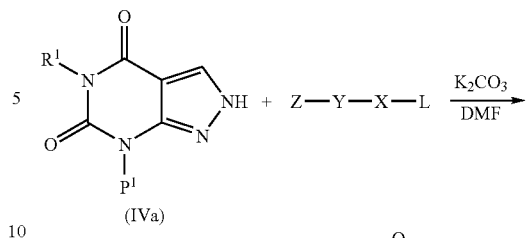

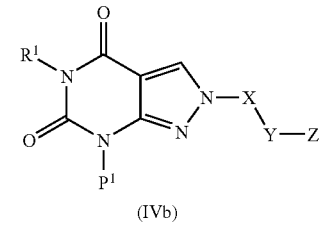

(IVb)

Intermediate IVc may be synthesized from a compound of IVb by removing the protective group $P^1$ with an appropriate method. For example, if $P^1$ is a PMB group, then it can be removed with CAN at room temperature:

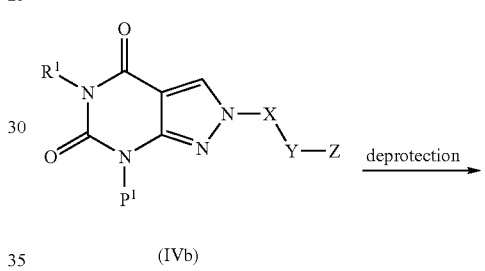

Intermediate IVd can be prepared by reacting a compound of IVc with for example a chlorinating compound such as $POCl_3$ and refluxed for about 2 days, or heated at 150–200° C. for about 10 min in a sealed vial with a microwave instrument and then cooled:

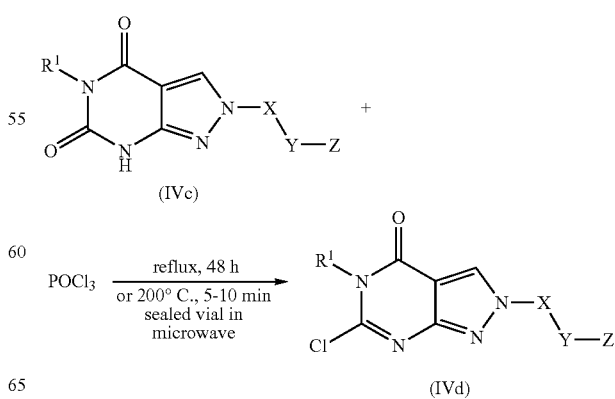

Intermediate IVe can be formed by reacting a compound of IVd with an amino alcohol under basic condition in a solvent such as DMF and heated overnight then cooled:

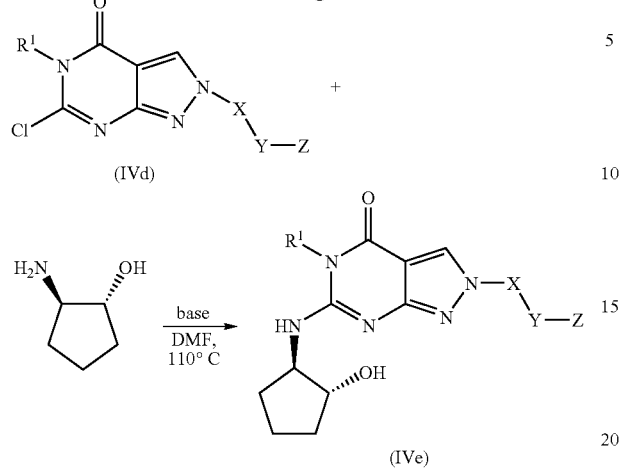

Compound IVf may be formed by reacting a compound of IVe with for example a dehydrating/halogenating agent such as SOCl$_2$ in a solvent such as CH$_2$Cl$_2$ at room temperature overnight or heated at 35° C. for about 4 hours, and then cooled.

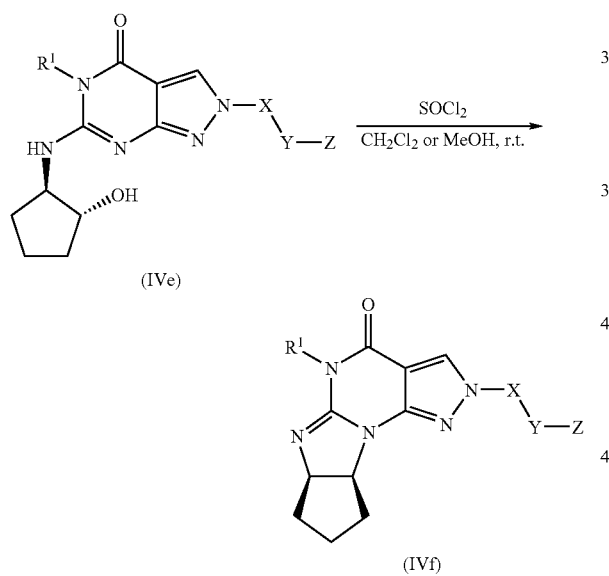

Compound IVg may be formed by reacting a compound of IVf with for example a halogenating agent such as NCS and a base such as LDA in a solvent such as THF at low temperature for several hours.

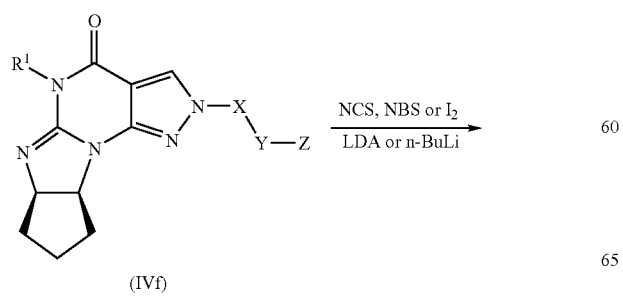

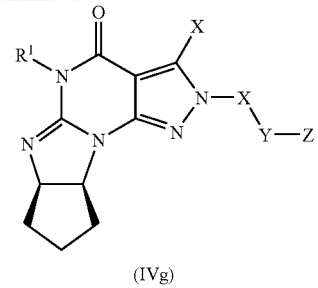

Compound Ia may be formed by reacting a compound of IVg with for example an amine such as aniline in the present of a catalyst such as Pd$_2$(dba)$_3$ in a solvent such as dioxane at 100° C. overnight.

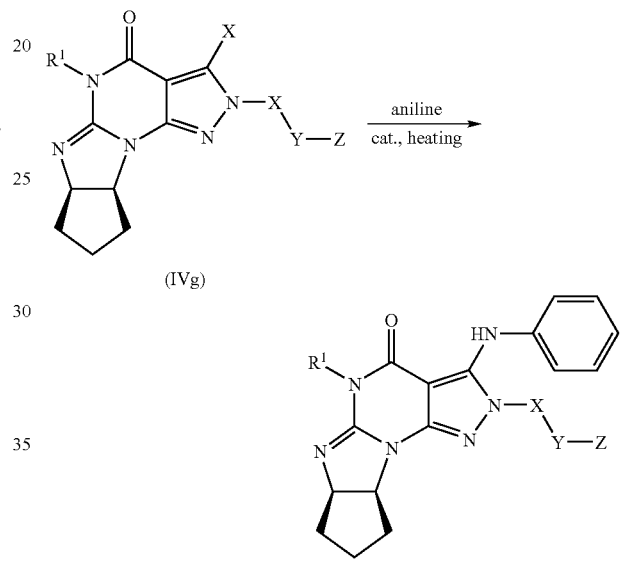

The invention thus provides methods of making Compounds of Formula I, for example, comprising (i) reacting a (6aR,9aS)-3-(phenylamino)-5-6a,7,8,9,9a-hexahydro-5-methyl-cyclopent[4,5]imidazo[1,2-a]pyrazolo[4,3-e]pyrimidin-4(1H or 2H)-one with a compound of formula Z—Y—X-L wherein L is a leaving group, e.g., halogen, mesylate, or tosylate, X, Y and Z are as defined above in Formula I, e.g., under basic conditions, for example wherein the (6aR,9aS)-3-(phenylamino)-5-6a,7,8,9,9a-hexahydro-5-methyl-cyclopent[4,5]imidazo[1,2-a]pyrazolo[4,3-e]pyrimidin-4(2H)-one is a compound of Formula IIK:

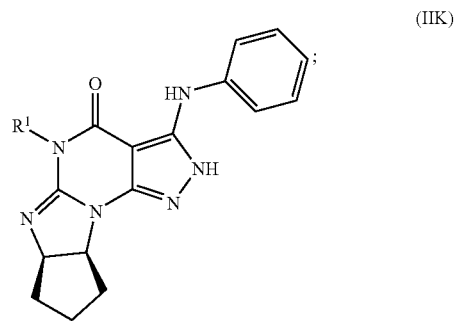

or
(ii) cyclization of a compound of Formula V

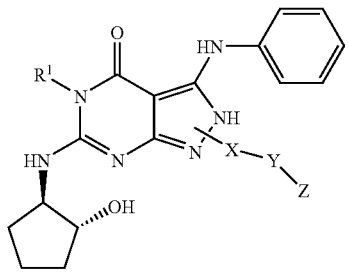

wherein, X, Y and Z are as defined above with reference to Formula I, e.g., using a dehydrating/halogentating agent, for example thionyl chloride;
and isolating the Compound of the Invention thus obtained.

Similarly, the invention also provides methods of making Compounds of Formula Q, for example, comprising:
(i) reacting a (6aR,9aS)-3-(phenylamino)-5-6a,7,8,9,9a-hexahydro-5-methyl-cyclopent[4,5]imidazo[1,2-a]pyrazolo[4,3-e]pyrimidin-4(1H or 2H)-one with a compound of formula Z—Y—X-L wherein L is a leaving group, e.g., halogen, mesylate, or tosylate, X, Y and Z are as defined above in Formula Q, e.g., under basic conditions, for example wherein the (6aR,9aS)-3-(phenylamino)-5-6a,7,8,9,9a-hexahydro-5-methyl-cyclopent[4,5]imidazo[1,2-a]pyrazolo[4,3-e]pyrimidin-4 (2H)-one is a compound of Formula QK:

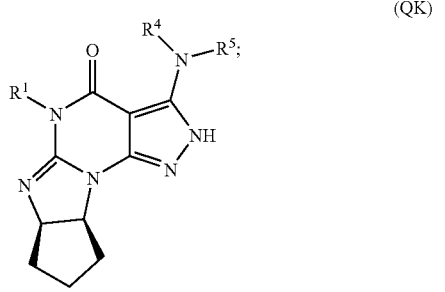

(QK)

or
(ii) cyclization of a compound of Formula QV

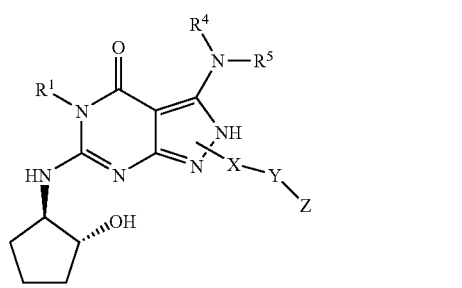

wherein, X, Y and Z are as defined above with reference to Formula Q, e.g., using a dehydrating/halogentating agent, for example thionyl chloride.

Methods of Using Compounds of the Invention

The Compounds of the Invention are useful in the treatment of diseases characterized by disruption of or damage to cAMP and cGMP mediated pathways, e.g., as a result of increased expression of PDE1 or decreased expression of cAMP and cGMP due to inhibition or reduced levels of inducers of cyclic nucleotide synthesis, such as dopamine and nitric oxide (NO). By preventing the degradation of cAMP and cGMP by PDE1B, thereby increasing intracellular levels of cAMP and cGMP, the Compounds of the Invention potentiate the activity of cyclic nucleotide synthesis inducers.

The invention provides methods of treatment of any one or more of the following conditions:
(i) Neurodegenerative diseases, including Parkinson's disease, restless leg, tremors, dyskinesias, Huntington's disease, Alzheimer's disease, and drug-induced movement disorders;
(ii) Mental disorders, including depression, attention deficit disorder, attention deficit hyperactivity disorder, bipolar illness, anxiety, sleep disorders, e.g., narcolepsy, cognitive impairment, dementia, Tourette's syndrome, autism, fragile X syndrome, psychostimulant withdrawal, and drug addiction;
(iii) Circulatory and cardiovascular disorders, including cerebrovascular disease, stroke, congestive heart disease, hypertension, pulmonary hypertension, and sexual dysfunction;
(iv) Respiratory and inflammatory disorders, including asthma, chronic obstructive pulmonary disease, and allergic rhinitis, as well as autoimmune and inflammatory diseases;
(v) Any disease or condition characterized by low levels of cAMP and/or cGMP (or inhibition of cAMP and/or cGMP signaling pathways) in cells expressing PDE1; and/or
(vi) Any disease or condition characterized by reduced dopamine D1 receptor signaling activity, comprising administering an effective amount of a Compound of the Invention, e.g., a compound according to any of Formula I or 1.57-1.87, to a human or animal patient in need thereof.

Similarly, the invention provides methods of treatment of any one or more of the following conditions:
(i) Neurodegenerative diseases, including Parkinson's disease, restless leg, tremors, dyskinesias, Huntington's disease, Alzheimer's disease, and drug-induced movement disorders;
(ii) Mental disorders, including depression, attention deficit disorder, attention deficit hyperactivity disorder, bipolar illness, anxiety, sleep disorders, e.g., narcolepsy, cognitive impairment, dementia, Tourette's syndrome, autism, fragile X syndrome, psychostimulant withdrawal, and drug addiction;
(iii) Circulatory and cardiovascular disorders, including cerebrovascular disease, stroke, congestive heart disease, hypertension, pulmonary hypertension, and sexual dysfunction;
(iv) Respiratory and inflammatory disorders, including asthma, chronic obstructive pulmonary disease, and allergic rhinitis, as well as autoimmune and inflammatory diseases;
(v) Any disease or condition characterized by low levels of cAMP and/or cGMP (or inhibition of cAMP and/or cGMP signaling pathways) in cells expressing PDE1; and/or
(vi) Any disease or condition characterized by reduced dopamine D1 receptor signaling activity, comprising administering an effective amount of a Compound of the Invention, e.g., a compound according to any of Formula Q or 1.1-1.56, or Formula (X), to a human or animal patient in need thereof.

In an especially preferred embodiment, the invention provides methods of treatment or prophylaxis for narcolepsy. In this embodiment, PDE 1 Inhibitors may be used as a sole therapeutic agent, but may also be used in combination or for co-administration with other active agents. Thus, the invention further comprises a method of treating narcolepsy comprising administering simultaneously, sequentially, or contemporaneously administering therapeutically effective amounts of
- (i) a PDE 1 Inhibitor, e.g., a compound according to any of Formula I or 1.57-1.87, and
- (ii) a compound to promote wakefulness or regulate sleep, e.g., selected from (a) central nervous system stimulants-amphetamines and amphetamine like compounds, e.g., methylphenidate, dextroamphetamine, methamphetamine, and pemoline; (b) modafinil, (c) antidepressants, e.g., tricyclics (including imipramine, desipramine, clomipramine, and protriptyline) and selective serotonin reuptake inhibitors (including fluoxetine and sertraline); and/or (d) gamma hydroxybutyrate (GHB).

in free or pharmaceutically acceptable salt form, to a human or animal patient in need thereof.

The invention also comprises a method of treating narcolepsy comprising administering simultaneously, sequentially, or contemporaneously administering therapeutically effective amounts of
- (i) a PDE 1 Inhibitor, e.g., a compound according to any of Formula Q or 1.1-1.56, or Formula (X) and
- (ii) a compound to promote wakefulness or regulate sleep, e.g., selected from (a) central nervous system stimulants-amphetamines and amphetamine like compounds, e.g., methylphenidate, dextroamphetamine, methamphetamine, and pemoline; (b) modafinil, (c) antidepressants, e.g., tricyclics (including imipramine, desipramine, clomipramine, and protriptyline) and selective serotonin reuptake inhibitors (including fluoxetine and sertraline); and/or (d) gamma hydroxybutyrate (GHB).

in free or pharmaceutically acceptable salt form, to a human or animal patient in need thereof.

In another embodiment, the invention provides methods of treatment or prophylaxis of a condition which may be alleviated by the enhancement of the progesterone signaling comprising administering an effective amount of a Compound of the Invention, e.g., a compound according to any of Formula 1.57-1.87 or Formula I, to a human or animal patient in need thereof. In still another embodiment, the invention further provides methods of treatment or prophylaxis of a condition which may be alleviated by the enhancement of the progesterone signaling comprising administering an effective amount of a Compound of the Invention, e.g., a compound according to any of Formula Q or 1.1-1.56, or Formula (X) to a human or animal patient in need thereof. Disease or condition that may be ameliorated by enhancement of progesterone signaling include, but are not limited to, female sexual dysfunction, secondary amenorrhea (e.g., exercise amenorrhoea, anovulation, menopause, menopausal symptoms, hypothyroidism), pre-menstrual syndrome, premature labor, infertility, for example infertility due to repeated miscarriage, irregular menstrual cycles, abnormal uterine bleeding, osteoporosis, autoimmune disease, multiple sclerosis, prostate enlargement, prostate cancer, and hypothyroidism. For example, by enhancing progesterone signaling, the PDE 1 inhibitors may be used to encourage egg implantation through effects on the lining of uterus, and to help maintain pregnancy in women who are prone to miscarriage due to immune response to pregnancy or low progesterone function. The novel PDE 1 inhibitors, e.g., as described herein, may also be useful to enhance the effectiveness of hormone replacement therapy, e.g., administered in combination with estrogen/estradiol/estriol and/or progesterone/progestins in postmenopausal women, and estrogen-induced endometrial hyperplasia and carcinoma. The methods of the invention are also useful for animal breeding, for example to induce sexual receptivity and/or estrus in a nonhuman female mammal to be bred.

In this embodiment, PDE 1 Inhibitors may be used in the foregoing methods of treatment or prophylaxis as a sole therapeutic agent, but may also be used in combination or for co-administration with other active agents, for example in conjunction with hormone replacement therapy. Thus, the invention further comprises a method of treating disorders that may be ameliorated by enhancement of progesterone signaling comprising administering simultaneously, sequentially, or contemporaneously administering therapeutically effective amounts of
- (i) a PDE 1 Inhibitor, e.g., a compound according to any of Formula 1.57-1.87 or Formula I, and
- (ii) a hormone, e.g., selected from estrogen and estrogen analogues (e.g., estradiol, estriol, estradiol esters) and progesterone and progesterone analogues (e.g., progestins)

in free or pharmaceutically acceptable salt form, to a human or animal patient in need thereof.

The invention also comprises a method of treating disorders that may be ameliorated by enhancement of progesterone signaling comprising administering simultaneously, sequentially, or contemporaneously administering therapeutically effective amounts of
- (i) a PDE 1 Inhibitor, e.g., a compound according to any of Formula Q, e.g., 1.1-1.56, or Formula (X) and
- (ii) a hormone, e.g., selected from estrogen and estrogen analogues (e.g., estradiol, estriol, estradiol esters) and progesterone and progesterone analogues (e.g., progestins)

in free or pharmaceutically acceptable salt form, to a human or animal patient in need thereof.

The invention also provides a method for enhancing or potentiating dopamine D1 intracellular signaling activity in a cell or tissue comprising contacting said cell or tissue with an amount of a Compound of the Invention, e.g., Formula Q, I, e.g., 1.1-1.56 or 1.57-1.87, or Formula (X), sufficient to inhibit PDE1B activity.

The invention also provides a method for enhancing or potentiating progesterone signaling activity in a cell or tissue comprising contacting said cell or tissue with an amount of a Compound of the Invention, e.g., Formula Q, I, e.g., 1.1-1.56 or 1.57-1.87, or Formula (X), sufficient to inhibit PDE1B activity.

The invention also provides a method for treating a PDE1-related, especially PDE1B-related disorder, a dopamine D1 receptor intracellular signaling pathway disorder, or disorders that may be alleviated by the enhancement of the progesterone signaling pathway in a patient in need thereof comprising administering to the patient an effective amount of a Compound of the Invention, e.g., Formula Q, I, e.g., 1.1-1.56 or 1.57-1.87, or Formula (X), that inhibits PDE1B, wherein PDE1B activity modulates phosphorylation of DARPP-32 and/or the GluR1 AMPA receptor.

The present invention also provides
(i) a Compound of the Invention, e.g., Formula Q, I, e.g., 1.1-1.56 or 1.57-1.87, or Formula (X), for use as a pharmaceutical, for example for use in any method or in the treatment of any disease or condition as hereinbefore set forth,
(ii) the use of a Compound of the Invention, e.g., Formula Q, I, e.g., 1.1-1.56 or 1.57-1.87, or Formula (X), in the manufacture of a medicament for treating any disease or condition as hereinbefore set forth,
(iii) a pharmaceutical composition comprising a Compound of the Invention, e.g., Formula Q, I, e.g., 1.1-1.56 or 1.57-1.87 or Formula (X), in combination or association with a pharmaceutically acceptable diluent or carrier, and
(iv) a pharmaceutical composition comprising a Compound of the Invention, e.g., Formula Q, I, e.g., 1.1-1.56 or 1.57-1.87, or Formula (X), in combination or association with a pharmaceutically acceptable diluent or carrier for use in the treatment of any disease or condition as hereinbefore set forth.

Therefore, the invention provides use of a Compound of the Invention, e.g., Formula Q, I, e.g., 1.1-1.56 or 1.57-1.87, or Formula (X), in free or pharmaceutically acceptable salt or prodrug form, or a Compound of the Invention in a pharmaceutical composition form, for the manufacture of a medicament for the treatment or prophylactic treatment of the following diseases: Parkinson's disease, restless leg, tremors, dyskinesias, Huntington's disease, Alzheimer's disease, and drug-induced movement disorders; depression, attention deficit disorder, attention deficit hyperactivity disorder, bipolar illness, anxiety, sleep disorder, narcolepsy, cognitive impairment, dementia, Tourette's syndrome, autism, fragile X syndrome, psychostimulant withdrawal, and/or drug addiction; cerebrovascular disease, stroke, congestive heart disease, hypertension, pulmonary hypertension, and/or sexual dysfunction; asthma, chronic obstructive pulmonary disease, and/or allergic rhinitis, as well as autoimmune and inflammatory diseases; and/or female sexual dysfunction, exercise amenorrhoea, anovulation, menopause, menopausal symptoms, hypothyroidism, pre-menstrual syndrome, premature labor, infertility, irregular menstrual cycles, abnormal uterine bleeding, osteoporosis, multiple sclerosis, prostate enlargement, prostate cancer, hypothyroidism, estrogen-induced endometrial hyperplasia or carcinoma; and/or any disease or condition characterized by low levels of cAMP and/or cGMP (or inhibition of cAMP and/or cGMP signaling pathways) in cells expressing PDE1, and/or by reduced dopamine D1 receptor signaling activity; and/or any disease or condition that may be ameliorated by the enhancement of progesterone signaling; comprising administering an effective amount of a Compound of the Invention, or a pharmaceutical composition comprising a Compound of the Invention, e.g., Formula Q, I, e.g., 1.1-1.56 or 1.57-1.87, or Formula (X), to a patient in need of such treatment.

The words "treatment" and "treating" are to be understood accordingly as embracing prophylaxis and treatment or amelioration of symptoms of disease as well as treatment of the cause of the disease Compounds of the Invention are in particular useful for the treatment of Parkinson's disease, narcolepsy and female sexual dysfunction.

Compounds of the Invention, e.g., Formula Q, I, e.g., 1.1-1.56 or 1.57-1.87, or Formula (X), may be used as a sole therapeutic agent, but may also be used in combination or for co-administration with other active agents. For example, as Compounds of the Invention potentiate the activity of D1 agonists, such as dopamine, they may be simultaneously, sequentially, or contemporaneously administered with conventional dopaminergic medications, such as levodopa and levodopa adjuncts (carbidopa, COMT inhibitors, MAO-B inhibitors), dopamine agonists, and anticholinergics, e.g., in the treatment of a patient having Parkinson's disease. In addition, the novel PDE 1 inhibitors, e.g., as described herein, may also be administered in combination with estrogen/estradiol/estriol and/or progesterone/progestins to enhance the effectiveness of hormone replacement therapy or treatment of estrogen-induced endometrial hyperplasia or carcinoma.

Dosages employed in practicing the present invention will of course vary depending, e.g. on the particular disease or condition to be treated, the particular Compound of the Invention used, the mode of administration, and the therapy desired. Compounds of the Invention may be administered by any suitable route, including orally, parenterally, transdermally, or by inhalation, but are preferably administered orally. In general, satisfactory results, e.g. for the treatment of diseases as hereinbefore set forth are indicated to be obtained on oral administration at dosages of the order from about 0.01 to 2.0 mg/kg. In larger mammals, for example humans, an indicated daily dosage for oral administration will accordingly be in the range of from about 0.75 to 150 mg, conveniently administered once, or in divided doses 2 to 4 times, daily or in sustained release form. Unit dosage forms for oral administration thus for example may comprise from about 0.2 to 75 or 150 mg, e.g. from about 0.2 or 2.0 to 50, 75 or 100 mg of a Compound of the Invention, together with a pharmaceutically acceptable diluent or carrier therefor.

Pharmaceutical compositions comprising Compounds of the Invention may be prepared using conventional diluents or excipients and techniques known in the galenic art. Thus oral dosage forms may include tablets, capsules, solutions, suspensions and the like.

EXAMPLES

Example 1

(6aR,9aS)-5,6a,7,8,9,9a-hexahydro-5-methyl-3-(phenylamino)-2-((tetrahydro-2H-pyran-4-yl)methyl)-cyclopent[4,5]imidazo[1,2-a]pyrazolo[4,3-e]pyrimidin-4(2H)-one

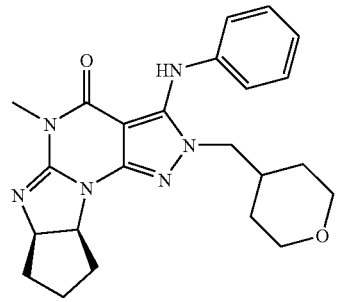

(a) 7-(4-Methoxybenzyl)-5-methyl-3-(phenylamino)-1H-pyrazolo[3,4-d]pyrimidine-4,6(5H,7H)-dione Phenyl isothiocyanate (3.9 mL, 32.7 mmol) is added to a suspension of 6-hydrazinyl-1-(4-methoxybenzyl)-3-methylpyrimidine-2,4(1H,3H)-dione (0.45 g, 1.6 mmol) in DMF (12 mL). The reaction mixture is heated at 120° C. for 40 hours, and then evaporated to remove solvent under reduced pressure. The residue is washed with hexanes, and then treated with MeOH (125 mL), and stored at −15° C. for 2 days to give a crystalline solid. The solid is recrystallized from $CH_3OH$-EtOAc to afford 2.5 g of product (Yield: 61%). $^1$H NMR (400 MHz, DMSO-$d_6$) δ 3.21 (s, 3H), 3.73 (s, 3H), 5.01 (s, 2H), 6.88-7.36 (m, 9H). MS (FAB) m/z 378.3 [M+H]$^+$.

(b) 5-Methyl-3-(phenylamino)-1H-pyrazolo[3,4-d]pyrimidine-4,6(5H,7H)-dione

To a solution of 7-(4-Methoxybenzyl)-5-methyl-3-(phenylamino)-1H-pyrazolo[3,4-d]pyrimidine-4,6(5H,7H)-dione (6.6 g, 17.5 mmol) in $CH_2Cl_2$ (200 mL) added TFA (30 mL) slowly at room temperature, followed by adding trifluoromethanesulfonic acid (10 mL) dropwise. After the reaction mixture is stirred at r.t. for 2 hours, solvent is removed under reduced pressure, and then 200 mL of 1N NaOH is added with cooling. The mixture is extracted with ethyl acetate five times, dried over $Na_2SO_4$, and then filtered. The filtrate is evaporated to dryness to give 4.3 g of crude product as white solids (Yield: 96%). MS (ESI) m/z 258.1 [M+H]$^+$.

(c) 6-Chloro-5-methyl-3-(phenylamino)-1H-pyrazolo[3,4-d]pyrimidin-4(5H)-one 5-methyl-3-(phenylamino)-1H-pyrazolo[3,4-d]pyrimidine-4,6(5H,7H)-dione (4.3 g, 16.7 mmol) is refluxed in $POCl_3$ (120 mL) for 2 days, and then $POCl_3$ is removed under reduced pressure. The residue is suspended in 100 mL of water and carefully adjusted to pH=1-2 with 7% $NH_4OH$ upon cooling. The mixture is then extracted with $CH_2Cl_2$ and MeOH (10:1, v/v) five times. The combined organic phase is washed with water, dried over $Na_2SO_4$, and then evaporated under reduced vacuum to give 3.3 g of crude product (Yield: 72%). MS (ESI) m/z 276.1 [M+H]$^+$.

(d) 6-((1R,2R)-2-hydroxycyclopentylamino)-5-methyl-3-(phenylamino)-2H-pyrazolo[3,4-d]pyrimidin-4(5H)-one A solution of 6-chloro-5-methyl-3-(phenylamino)-1H-pyrazolo[3,4-d]pyrimidin-4(5H)-one (3.3 g, 12 mmol), (1R,2R)-2-aminocyclopentanol hydrochloride (2 g, 14.4 mmol) and DIPEA (4.6 mL, 27 mmol) in DMF (25 mL) is heated at 120° C. for 5 hours. Solvent is removed under reduced pressure. The residue is dissolved in $CH_2Cl_2$ and MeOH (10:1, v/v), and then washed with water three times. The solution is dried over $MgSO_4$ and evaporated to dryness to give 3.5 g of crude product. MS (ESI) m/z 341.2 [M+H]$^+$.

(e) (6aR,9aS)-5,6a,7,8,9,9a-hexahydro-5-methyl-3-(phenylamino)-cyclopent[4,5]imidazo[1,2-a]pyrazolo[4,3-e]pyrimidin-4(2H)-one 2.0 M solution of thionyl chloride in $CH_2Cl_2$ (7.5 mL, 15.4 mmol) is added dropwise to a solution of 6-((1R,2R)-2-hydroxycyclopentylamino)-5-methyl-3-(phenylamino)-2H-pyrazolo[3,4-d]pyrimidin-4(5H)-one (3.5 g, 10.3 mmol) in $CH_2Cl_2$ (30 mL) at room temperature. After the completion of the addition, the reaction mixture is stirred at r.t. for 2 h. Solvent and excess $SOCl_2$ are removed under reduced pressure. The residue is suspended in water (100 mL), and then carefully neutralized with 7% ammonium hydroxide (5 mL) to pH=6.5-7. The mixture is extracted with $CH_2Cl_2$ and MeOH (10:1, v/v) five times. The combined organic phase is washed with water, dried over $Na_2SO_4$, and then evaporated under reduced vacuum to give 2.9 g of crude product. MS (ESI) m/z 323.2 [M+H]$^+$.

(6aR,9aS)-5,6a,7,8,9,9a-hexahydro-5-methyl-3-(phenylamino)-2-((tetrahydro-2H-pyran-4-yl)methyl)-cyclopent[4,5]imidazo[1,2-a]pyrazolo[4,3-e]pyrimidin-4(2H)-one A mixture of (6aR,9aS)-5,6a,7,8,9,9a-hexahydro-5-methyl-3-(phenylamino)-cyclopent[4,5]imidazo[1,2-a]pyrazolo[4,3-e]pyrimidin-4(2H)-one (50 mg, 0.155 mmol), 4-(iodomethyl)-tetrahydro-2H-pyran (70 mg, 0.310 mmol), and $Cs_2CO_3$ (101 mg, 0.310 mmol) in DMF (1 mL) is heated in microwave at 140° C. for 30 min. After cooling, the mixture is filtered through a 0.45 μM microfilter, and the filtrate is purified by a semi-preparative HPLC to give pure product as white powder. MS (ESI) m/z 421.2 [M+H]$^+$.

Example 2

(6aR,9aS)-5,6a,7,8,9,9a-hexahydro-5-methyl-3-(phenylamino)-1-((tetrahydro-2H-pyran-4-yl)methyl)-cyclopent[4,5]imidazo[1,2-a]pyrazolo[4,3-e]pyrimidin-4(1H)-one

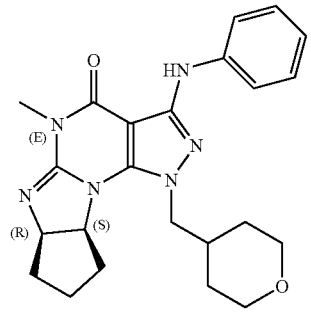

A mixture of (6aR,9aS)-5,6a,7,8,9,9a-hexahydro-5-methyl-3-(phenylamino)-cyclopent[4,5]imidazo[1,2-a]pyrazolo[4,3-e]pyrimidin-4(2H)-one (50 mg, 0.155 mmol), 4-(iodomethyl)-tetrahydro-2H-pyran (70 mg, 0.310 mmol), and $Cs_2CO_3$ (101 mg, 0.310 mmol) in DMF (1 mL) is heated in microwave at 140° C. for 30 min. After cooling, the mixture is filtered through a 0.45 μm microfilter, and the filtrate is purified by a semi-preparative HPLC to give pure product as white powder. MS (ESI) m/z 421.2 [M+H]$^+$.

Example 3

(6aR,9aS)-5,6a,7,8,9,9a-hexahydro-5-methyl-3-(phenylamino)-1-(3-(dimethylamino)-2-methylpropyl)-cyclopent[4,5]imidazo[1,2-a]pyrazolo[4,3-e]pyrimidin-4(1H)-one

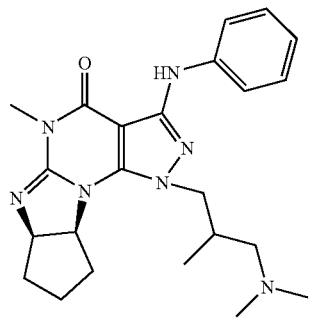

The synthesis method is analogous to example 2 wherein 3-chloro-N,N,2-trimethylpropan-1-amine is added instead of

Example 4

(6aR,9aS)-5,6a,7,8,9,9a-hexahydro-5-methyl-3-(phenylamino)-1-(cyclopentylmethyl)-cyclopent[4,5]imidazo[1,2-a]pyrazolo[4,3-e]pyrimidin-4(1H)-one

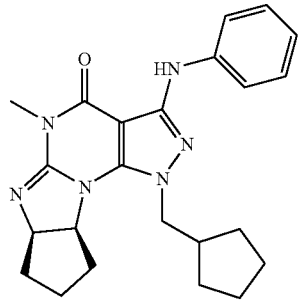

The synthesis method is analogous to example 2 wherein cyclopentylmethyl iodide is added instead of 4-(iodomethyl)-tetrahydro-2H-pyran. MS (ESI) m/z 405.2 [M+H]$^+$.

Example 5

(6aR,9aS)-5,6a,7,8,9,9a-hexahydro-5-methyl-3-(phenylamino)-2-(cyclopentylmethyl)-cyclopent[4,5]imidazo[1,2-a]pyrazolo[4,3-e]pyrimidin-4(2H)-one

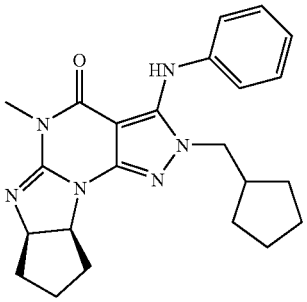

The synthesis method is analogous to example 1 wherein cyclopentylmethyl iodide is added instead of 4-(iodomethyl)-tetrahydro-2H-pyran. MS (ESI) m/z 405.2 [M+H]$^+$.

Example 6

(6aR,9aS)-5,6a,7,8,9,9a-hexahydro-5-methyl-3-(phenylamino)-1-(3-phenylprop-2-ynyl)-cyclopent[4,5]imidazo[1,2-a]pyrazolo[4,3-e]pyrimidin-4(1H)-one

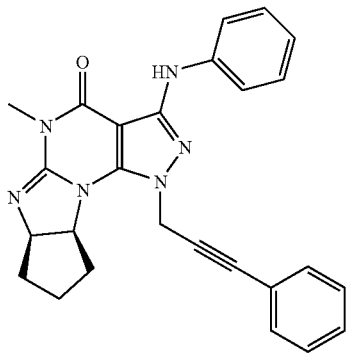

The synthesis method is analogous to example 2 wherein (3-bromoprop-1-ynyl)benzene is added instead of 4-(iodomethyl)-tetrahydro-2H-pyran. MS (ESI) m/z 437.2 [M+H]$^+$.

Example 7

(6aR,9aS)-5,6a,7,8,9,9a-hexahydro-5-methyl-3-(phenylamino)-1-(4-acetylphenethyl)-cyclopent[4,5]imidazo[1,2-a]pyrazolo[4,3-e]pyrimidin-4(1H)-one

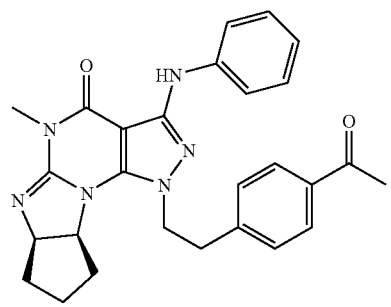

The synthesis method is analogous to example 2 wherein 1-(4-(2-chloroethyl)phenyl)ethanone is added instead of 4-(iodomethyl)-tetrahydro-2H-pyran. MS (ESI) m/z 469.1 [M+H]$^+$.

Example 8

(6aR,9aS)-5,6a,7,8,9,9a-hexahydro-5-methyl-3-(phenylamino)-2-(4-acetylphenethyl)-cyclopent[4,5]imidazo[1,2-a]pyrazolo[4,3-e]pyrimidin-4(2H)-one

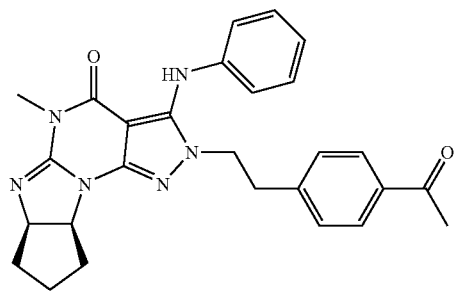

The synthesis method is analogous to example 1 wherein 1-(4-(2-chloroethyl)phenyl)ethanone is added instead of 4-(iodomethyl)-tetrahydro-2H-pyran. MS (ESI) m/z 469.2 [M+H]$^+$.

Example 9

(6aR,9aS)-5,6a,7,8,9,9a-hexahydro-5-methyl-3-(phenylamino)-1-(3-fluoro-4-(2,2,2-trifluoroacetyl)benzyl)-cyclopent[4,5]imidazo[1,2-a]pyrazolo[4,3-e]pyrimidin-4(1H)-one

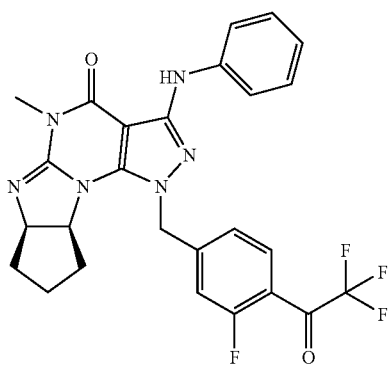

The synthesis method is analogous to example 2 wherein 1-(4-(bromomethyl)-2-fluorophenyl)-2,2,2-trifluoroethanone is added instead of 4-(iodomethyl)-tetrahydro-2H-pyran. MS (ESI) m/z 527.2 [M+H]$^+$.

Example 10

(6aR,9aS)-5,6a,7,8,9,9a-hexahydro-5-methyl-3-(phenylamino)-2-(3-fluoro-4-(2,2,2-trifluoroacetyl)benzyl)-cyclopent[4,5]imidazo[1,2-a]pyrazolo[4,3-e]pyrimidin-4(2H)-one

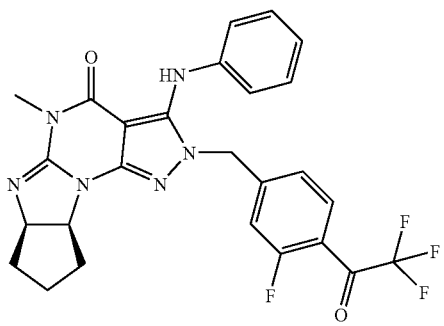

The synthesis method is analogous to example 1 wherein 1-(4-(bromomethyl)-2-fluorophenyl)-2,2,2-trifluoroethanone is added instead of 4-(iodomethyl)-tetrahydro-2H-pyran. MS (ESI) m/z 527.2 [M+H]$^+$.

Example 11

(6aR,9aS)-5,6a,7,8,9,9a-hexahydro-5-methyl-3-(phenylamino)-1-(4-(trifluoromethyl)phenethyl)-cyclopent[4,5]imidazo[1,2-a]pyrazolo[4,3-e]pyrimidin-4(1H)-one

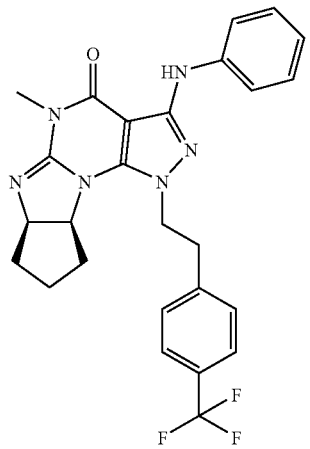

The synthesis method is analogous to example 2 wherein 1-(2-bromoethyl)-4-(trifluoromethyl)benzene is added instead of 4-(iodomethyl)-tetrahydro-2H-pyran. MS (ESI) m/z 495.2 [M+H]$^+$.

Example 12

(6aR,9aS)-5,6a,7,8,9,9a-hexahydro-5-methyl-3-(phenylamino)-2-(4-(trifluoromethyl)phenethyl)-cyclopent[4,5]imidazo[1,2-a]pyrazolo[4,3-e]pyrimidin-4(2H)-one

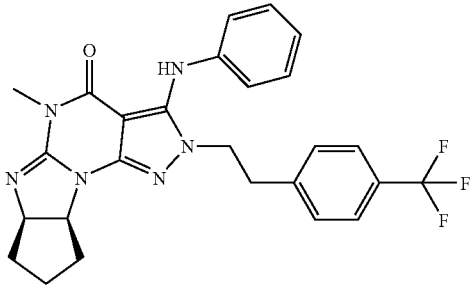

The synthesis method is analogous to example 1 wherein 1-(2-bromoethyl)-4-(trifluoromethyl)benzene is added instead of 4-(iodomethyl)-tetrahydro-2H-pyran. MS (ESI) m/z 495.2 [M+H]$^+$.

Example 13

(6aR,9aS)-5,6a,7,8,9,9a-hexahydro-5-methyl-3-(phenylamino)-2-(bromo(4-(5-fluoropyridin-2-yl)phenyl)methyl)-cyclopent[4,5]imidazo[1,2-a]pyrazolo[4,3-e]pyrimidin-4(2H)-one

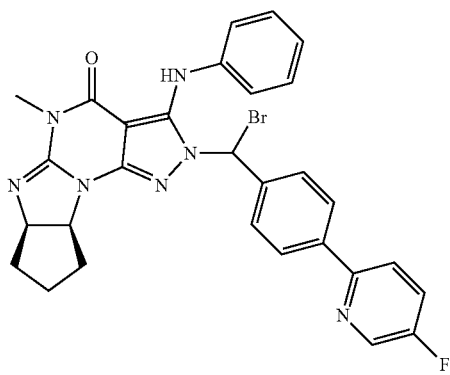

A mixture of (6aR,9aS)-5,6a,7,8,9,9a-hexahydro-5-methyl-3-(phenylamino)-cyclopent[4,5]imidazo[1,2-a]pyrazolo[4,3-e]pyrimidin-4(2H)-one (35 mg, 0.109 mmol), 2-(4-(dibromomethyl)phenyl)-5-fluoropyridine, and $K_2CO_3$ (15 mg, 0.109 mmol) in DMF (3 mL) is stirred at room temperature overnight. The mixture is filtered through a 0.45 μm microfilter, and the filtrate is purified by a semi-preparative HPLC to give product as white powder. MS (ESI) m/z 585.9 [M+H]$^+$.

Example 14

(6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(21)-one

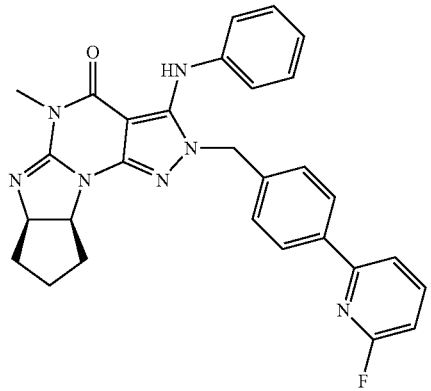

This compound may be made using similar method as in example 13 wherein 2-(4-(bromomethyl)phenyl)-6-fluoropyridine may be used instead of 2-(4-(dibromomethyl)phenyl)-5-fluoropyridine.

Example 15

Measurement of PDE1B Inhibition In Vitro Using IMAP Phosphodiesterase Assay Kit Phosphodiesterase 1B (PDE1B) is a calcium/calmodulin dependent phosphodiesterase enzyme that converts cyclic guanosine monophosphate (cGMP) to 5'-guanosine monophosphate (5'-GMP). PDE can also convert a modified cGMP substrate, such as the fluorescent molecule cGMP-fluorescein, to the corresponding GMP-fluorescein. The generation of GMP-fluorescein from cGMP-fluorescein can be quantitated, using, for example, the IMAP (Molecular Devices, Sunnyvale, Calif.) immobilized-metal affinity particle reagent.

Briefly, the IMAP reagent binds with high affinity to the free 5'-phosphate that is found in GMP-fluorescein and not in cGMP-fluorescein. The resulting GMP-fluorescein-IMAP complex is large relative to cGMP-fluorescein. Small fluorophores that are bound up in a large, slowly tumbling, complex can be distinguished from unbound fluorophores, because the photons emitted as they fluoresce retain the same polarity as the photons used to excite the fluorescence.

In the phosphodiesterase assay, cGMP-fluorescein, which cannot be bound to IMAP, and therefore retains little fluorescence polarization, is converted to GMP-fluorescein, which, when bound to IMAP, yields a large increase in fluorescence polarization (Δmp). Inhibition of phosphodiesterase, therefore, is detected as a decrease in Δmp.

Enzyme Assay

Materials: All chemicals are available from Sigma-Aldrich (St. Louis, Mo.) except for IMAP reagents (reaction buffer, binding buffer, FL-GMP and IMAP beads), which are available from Molecular Devices (Sunnyvale, Calif.).

Assay: 3',5'-cyclic-nucleotide-specific bovine brain phosphodiesterase (Sigma, St. Louis, Mo.) is reconstituted with 50% glycerol to 2.5 U/ml. One unit of enzyme will hydrolyze 1.0 μmole of 3',5'-cAMP to 5'-AMP per min at pH 7.5 at 30° C. One part enzyme is added to 1999 parts reaction buffer (30 μM $CaCl_2$, 10 U/ml of calmodulin (Sigma P2277), 10 mM Tris-HCl pH 7.2, 10 mM $MgCl_2$, 0.1% BSA, 0.05% $NaN_3$) to yield a final concentration of 1.25 mU/ml. 99 μl of diluted enzyme solution is added into each well in a flat bottom 96-well polystyrene plate to which 1 μl of test compound dissolved in 100% DMSO is added. The compounds are mixed and pre-incubated with the enzyme for 10 min at room temperature.

The FL-GMP conversion reaction is initiated by combining 4 parts enzyme and inhibitor mix with 1 part substrate solution (0.225 μM) in a 384-well microtiter plate. The reaction is incubated in dark at room temperature for 15 min. The reaction is halted by addition of 60 μl of binding reagent (1:400 dilution of IMAP beads in binding buffer supplemented with 1:1800 dilution of antifoam) to each well of the 384-well plate. The plate is incubated at room temperature for 1 hour to allow IMAP binding to proceed to completion, and then placed in an Envision multimode microplate reader (PerkinElmer, Shelton, Conn.) to measure the fluorescence polarization (Δmp).

A decrease in GMP concentration, measured as decreased Δmp, is indicative of inhibition of PDE activity. $IC_{50}$ values are determined by measuring enzyme activity in the presence of 8 to 16 concentrations of compound ranging from 0.0037 nM to 80,000 nM and then plotting drug concentration versus ΔmP, which allows $IC_{50}$ values to be estimated using nonlinear regression software (XLFit; IDBS, Cambridge, Mass.).

The Compounds of the Invention are selected and tested in an assay as described or similarly described herein for PDE1 inhibitory activity, which compounds generally have $IC_{50}$ values of less than 1 μM, e.g., the Compounds of formulae 1.54 and 1.55 generally have $IC_{50}$ values of less than 250 nM.

Example 16

PDE1 Inhibitor Effect on Sexual Response in Female Rats

The effect of PDE1 inhibitors on Lordosis Response in female rats is measured as described in Mani, et al., Science (2000) 287: 1053. Ovariectomized and cannulated wild-type rats are primed with 2 μg estrogen followed 24 hours later by intracerebroventricular (icv) injection of progesterone (2 μg), PDE1 inhibitors of the present invention (0.1 mg, 1.0 mg or 2.5 mg) or sesame oil vehicle (control). The rats are tested for lordosis response in the presence of male rats. Lordosis response is quantified by the lordosis quotient (LQ=number of lordosis/10 mounts×100). It will be observed that the LQ for estrogen-primed female rats receiving compounds of the present invention, at 0.1 mg, will generally be similar to estrogen-primed rats receiving progesterone and higher than for estrogen-primed rats receiving vehicle.

What is claimed is:

1. The compound (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one according to the following formula:

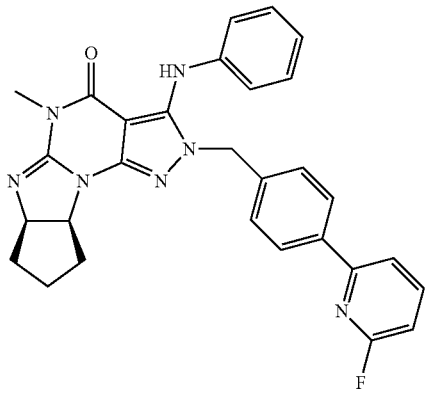

in free or salt form.

2. The compound according to claim 1, wherein the salt is a pharmaceutically acceptable salt.

3. A pharmaceutical composition comprising the compound according to claim 2, in admixture with a pharmaceutically acceptable diluent or carrier.

* * * * *